United States Patent
Alexson et al.

(10) Patent No.: US 9,678,186 B2
(45) Date of Patent: *Jun. 13, 2017

(54) PROBE FOR MAGNETIC RESONANCE FORCE MICROSCOPY AND METHOD THEREOF

(71) Applicant: The United States of America as Represented by the Secretary of the Army, Washington, DC (US)

(72) Inventors: Dimitri Arthur Alexson, Fairfax, VA (US); Doran Dakota Smith, Rockville, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 1171 days.

This patent is subject to a terminal disclaimer.

(21) Appl. No.: 13/755,115

(22) Filed: Jan. 31, 2013

(65) Prior Publication Data

US 2013/0193970 A1 Aug. 1, 2013

Related U.S. Application Data

(63) Continuation-in-part of application No. 13/361,056, filed on Jan. 30, 2012, now Pat. No. 9,128,157.

(51) Int. Cl.
*G01V 3/00* (2006.01)
*G01R 33/46* (2006.01)
(Continued)

(52) U.S. Cl.
CPC ............ *G01R 33/46* (2013.01); *G01N 24/08* (2013.01); *G01Q 60/52* (2013.01); *G01R 33/323* (2013.01); *G01R 33/34053* (2013.01)

(58) Field of Classification Search
CPC ...................................................... G01Q 60/52
(Continued)

(56) References Cited

U.S. PATENT DOCUMENTS

| | | | |
|---|---|---|---|
| 6,181,131 B1* | 1/2001 | Bruland | G01Q 60/52 324/300 |
| 9,128,157 B2* | 9/2015 | Smith | G01R 33/323 |
| 2010/0301854 A1* | 12/2010 | Rugar | B82Y 35/00 324/307 |

OTHER PUBLICATIONS

Marohn, John, et al. "An Optimal Magnetic Tip Configuration for Magnetic-Resonance Force Microscopy of Microscale Buried Features" Applied Physics Letters, vol. 73, No. 25, Dec. 21, 1998, pp. 3778-3780.

(Continued)

*Primary Examiner* — Louis Arana
(74) *Attorney, Agent, or Firm* — Lawrence E. Anderson

(57) ABSTRACT

A probe for use in Magnetic Resonance Force Microscopy (MRFM) to provide an image of a sample comprising: a magnetic field source adapted to orient the spin of the nuclei in a sample; a detector capable of detecting a magnetic field comprising an oscillator; at least one conductor substantially surrounding the oscillator for forming a RF antenna for transmitting a radio frequency electromagnetic field; whereby the at least one conductor transmits a radio frequency electromagnetic field that influences the nuclei in the sample, and whereby the detector detects how the nuclei are influenced through the oscillations of the oscillator to provide identification information concerning the content of the sample. Also included is a method for magnetic resonance force microscopy of a sample.

19 Claims, 17 Drawing Sheets

(51) Int. Cl.
*G01Q 60/52* (2010.01)
*G01N 24/08* (2006.01)
*G01R 33/32* (2006.01)
*G01R 33/34* (2006.01)

(58) Field of Classification Search
USPC .................................... 324/318, 322, 309
See application file for complete search history.

(56) References Cited

OTHER PUBLICATIONS

Smith, Doran, et al. "Detailed Description of a Compact Cryogenic Magnetic Resonance Force Microscope", American Institute of Physics, Review of Scientific Instruments, vol. 72, No. 4 Apr. 2001, pp. 2080-2089,doi: 10.1063/1.1357230.
Alexson, Dimitri A., et al. "Observation of Real Time Magnetization Inversion-recovery Using the SPAM Geometry and the CERMIT Protocol," ARL-TR-5742, U.S. Army Research Laboratory, Sep. 2011.

\* cited by examiner

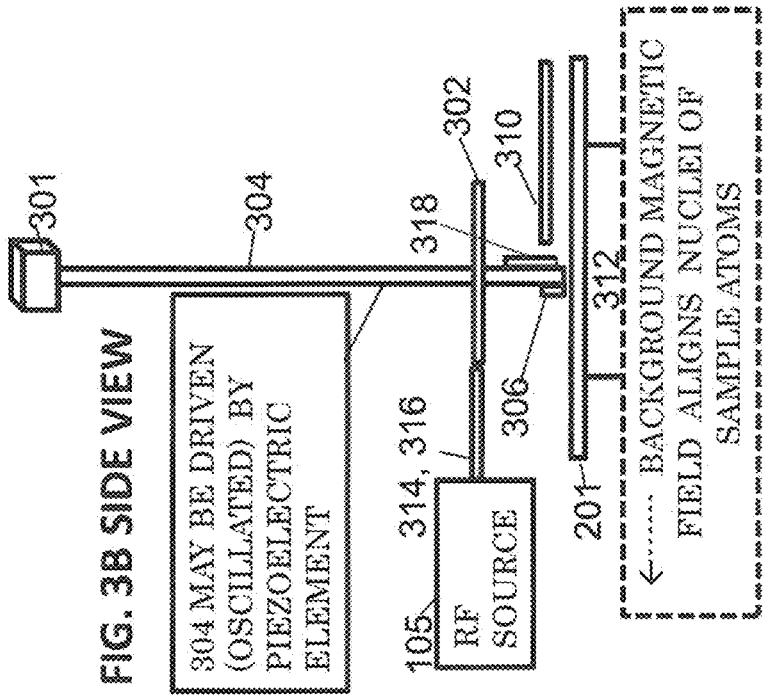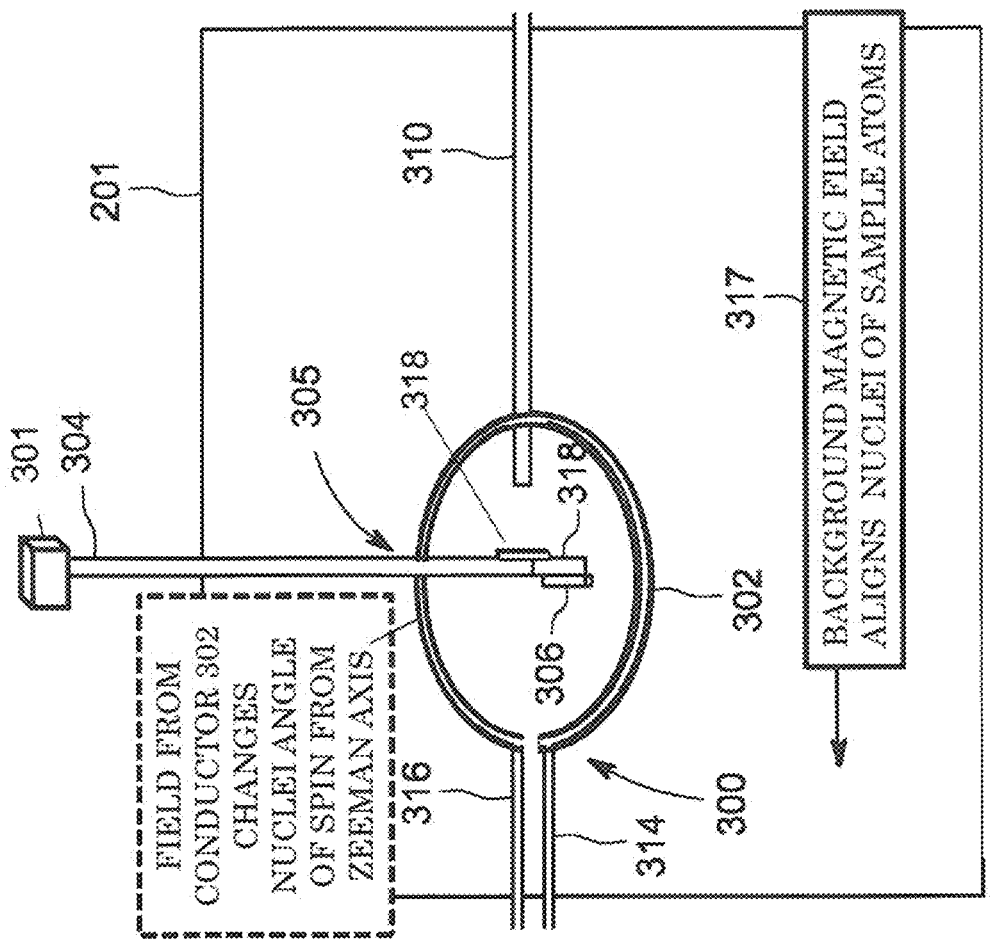

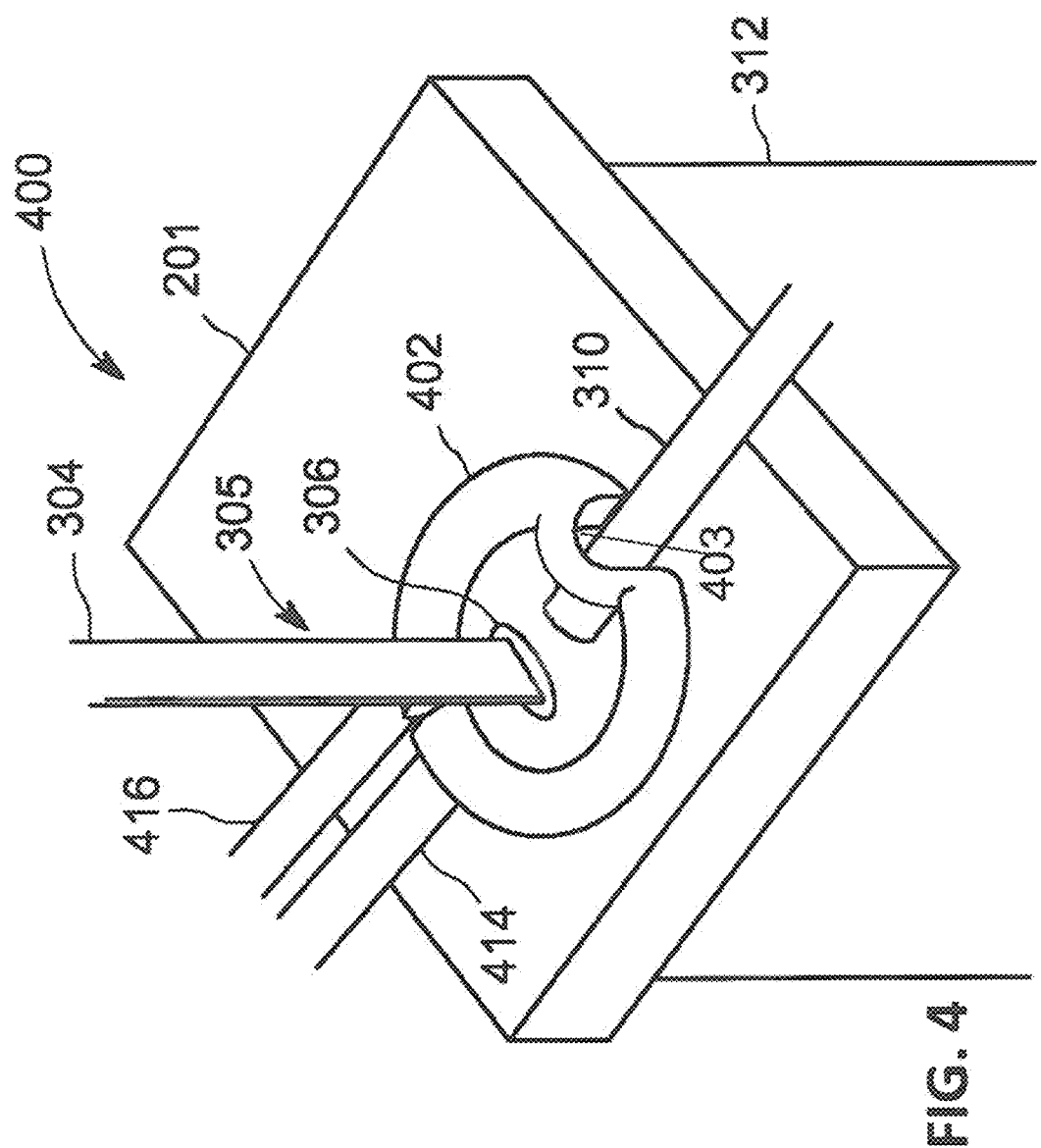

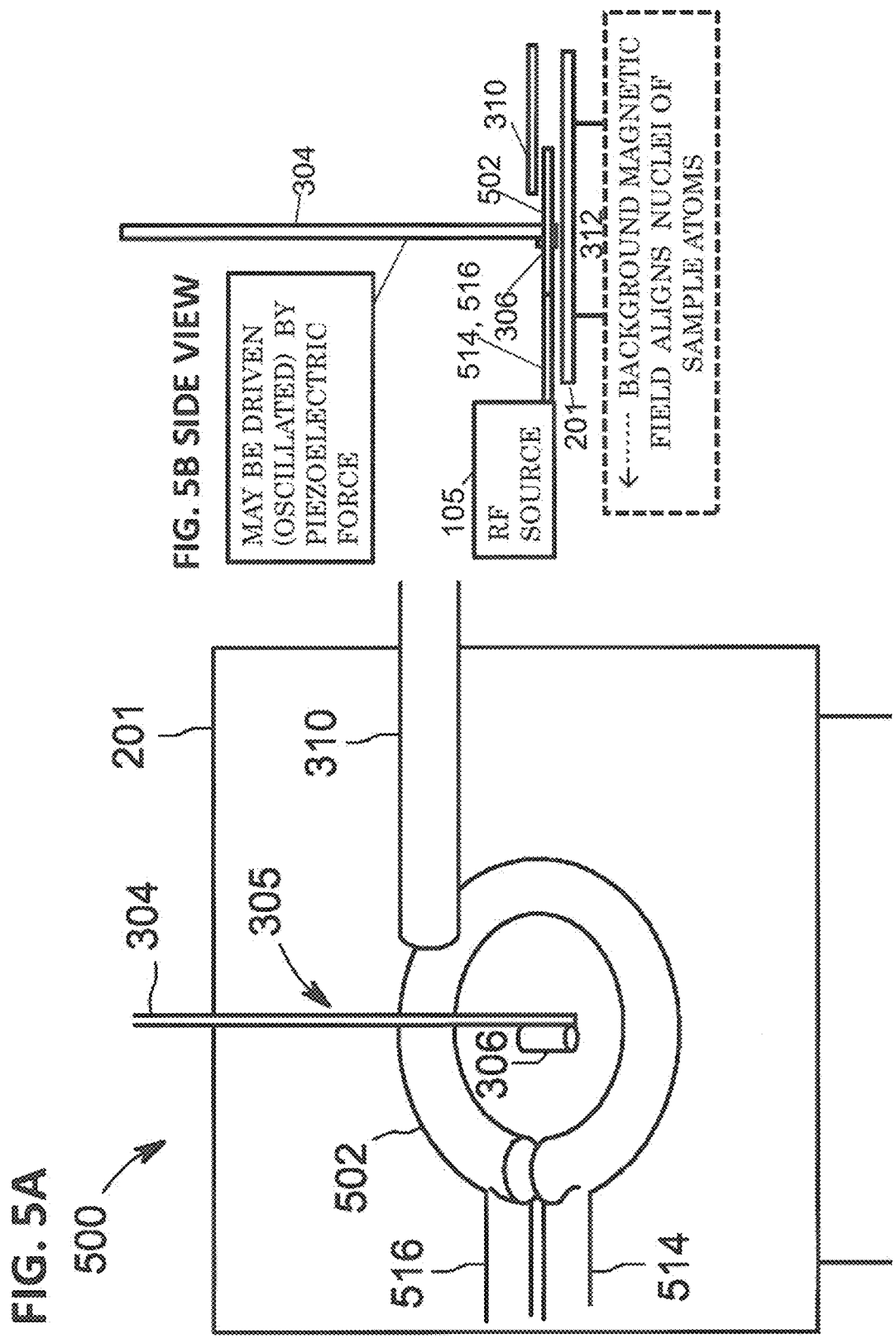

PROBE FOR MAGNETIC RESONANCE FORCE MICROSCOPY AND METHOD THEREOF

STATEMENT OF GOVERNMENT INTEREST

The embodiments herein may be manufactured, used, and/or licensed by or for the United States Government without the payment of royalties thereon.

CROSS REFERENCE TO RELATED APPLICATIONS

The present application claims priority to U.S. application Ser. No. 13/361,056 "Surfaced Scanning Radio Frequency Antenna for Magnetic Resonance Force Microscopy" (ARL 08-09) by co-inventor herein, Dr. Doran Smith, filed on Jan. 30, 2012, herein incorporated by reference.

BACKGROUND OF THE INVENTION

Magnetic resonance force microscopy (MRFM) is an imaging technique for nanometer scale magnetic resonance images (MRI) and a spectroscopic technique for determining the environment of a nuclear or electron spin. MRFM technology maybe used in research in biological cells and molecules, biotechnology, advanced nano-materials, inorganic and organic semiconductor devices and new spin physics. The sensitivity obtained using an MRFM microscope may be 10 billion times better than a medical MRI used in hospitals. MRFM combines two technologies: (1) mechanical detection and (2) magnetic resonance. The mechanical detection referred to is the attraction between two magnets, one of which may be attached to a cantilever, which causes the cantilever to change its amplitude or frequency depending on the MRFM protocol in use. The two magnets are a magnetic particle and a sample's magnetic moments, arising from either the nuclei or electrons in the sample. Both methods may be used in MRFM.

SUMMARY OF THE INVENTION

A preferred embodiment of the present invention comprises a probe for use in Magnetic Resonance Force Microscopy (MRFM) to provide an image or spectroscopy of a sample comprising: a magnetic field source adapted to orient the spin of the nuclei in a sample; a detector capable of detecting a magnetic field and/or magnetic field gradient comprising an oscillator; at least one conductor substantially surrounding the oscillator for forming a RF antenna for transmitting a radio frequency electromagnetic field; whereby the at least one conductor transmits a radio frequency electromagnetic field that influences the nuclei in the sample, and whereby the detector detects how the nuclei are influenced through the oscillations of the longitudinal oscillator to provide identification information concerning the content of the sample.

Optionally, the oscillator may be a longitudinal oscillator operating to detect the change in the angle of the spin from the Zeeman axis of the sample's nuclei in response to the RF field, the magnetic field source may be a magnetic field generator; and the plurality of conductors may comprise at least two coils mounted on a silicon substrate having a hole therein to provide the longitudinal oscillator access to a sample's surface; such that the at least two coils are adapted to be connected to an RF source.

Optionally, the detector may comprise an optical fiber adapted to transmit a laser beam; and the oscillator may comprises a magnetic particle and a reflecting surface which reflects light from a laser beam into the optical fiber to create an interferometer which is used to determine the change in the angle of spin from the Zeeman axis of the sample's nuclei which, in turn, provides information relating to the composition of the sample.

Optionally, upon application of an RF pulse sequence to the at least one conductor, the magnetic moments of the sample's nuclei may be rotated so as to reverse the direction of the magnetic moments in the sample's nuclei, and, as the magnetic moments in the sample nuclei are rotated, the oscillator resonates at a measurable frequency which is correlated to the composition of the sample.

Optionally, the at least one conductor comprise a series of coils each having first and second terminals which are adapted to be connected to a radio frequency generating source; whereby the sample's nuclei may be concurrently subjected to differing radio frequencies.

Optionally, the at least one conductor is mounted on a substrate which surrounds the oscillator, the substrate having a hole therein for receiving the oscillator.

Optionally, the at least one conductor may be formed on the substrate in the form of a spiral having a plurality of turns.

Another preferred embodiment of the probe for scanning the surface of a sample using magnetic resonance force microscopy comprises: a magnetic field source for producing a magnetic field; a magnetic sensor comprising a magnetic particle and a support, the magnetic particle being operatively connected to the support; an RF antenna at least partially surrounding the magnetic sensor for emitting an RF magnetic field across a portion of the sample; the RF antenna comprising a plurality of loops, and an optical sensor, positioned proximate the magnetic sensor, for detecting displacement of the support element, whereby the magnetic field from the magnetic field source operates to align the magnetic moments of the sample's nuclei or electrons and RF magnetic field operates to vary the alignment of the magnetic moments of the sample's nuclei or electrons, the magnetic sensor operating to respond to the variation in the alignments of the magnetic moments and displace the support element, the optical sensor operating to sense the displacement of the support element to thereby provide information as to the variance of the alignment of the sample's magnetic moments and thereby provide information as to the composition of the sample.

Optionally, the RF antenna comprises a substantially closed loop of wire surrounding the magnetic sensor. Optionally, the RF antenna comprises a plurality of coils surrounding the magnetic sensor. Optionally, the optical sensor is located between the RF antenna and the sample.

Optionally, the support is a cantilever, and wherein the magnetic particle responds to the nuclei or electrons of the sample causing the cantilever to oscillate and resonate at particular frequencies which provide information as to the identification of the sample's content. The magnetic particle may be a ferro-magnetic, paramagnetic, or superpara-magnetic particle.

A preferred methodology comprises a method for magnetic resonance force microscopy of a sample comprising:

providing a probe adapted to scan a surface of an arbitrarily sized sample, the probe comprising a support;

proving a magnetic sensor operatively associated with the support;

providing an RF antenna, at least partially surrounding the magnetic sensor, for emitting an RF magnetic field across at least a portion of the sample; the RF antenna adapted to be connected to an RF source for pulsing RF signals to the sample;

providing an optical sensor, positioned proximate to the magnetic sensor, for detecting displacement of the support element; the optical sensor comprising an interferometer for measuring displacement of the support; and providing a magnetic field source for generating a background magnetic field for the probe;

determining information concerning the sample by pulsing an RF field through the RF antenna and, using the optical sensor, measuring the movement of the support.

Optionally, the preferred method may comprise an RF antenna that forms at least one substantially closed loop of wire substantially surrounding the magnetic sensor, and the support may comprise a reflective surface which reflects light from the optical sensor to form an interferometer, the interferometer's laser beams contain information that can be extracted to providing information as to the composition of the sample.

Optionally, the method includes an RF antenna comprising a plurality of loops substantially surrounding the magnetic sensor. The loops may be irregularly shaped, polygonal, or substantially circular. The method may further include a display for displaying an image of the atomic level structure of the sample. Optionally, the support element may be adapted to be coupled to the sample.

Optionally, the method may comprise a support which comprises silicon configured as a cantilever, and the magnetic sensor may be a magnetic particle operatively associated with the cantilever. The optical sensor may comprise a laser and laser interferometry may be used to track the motion of the cantilever which vibrates as magnetic spins in the nuclei or electrons of the sample interact with the magnetic particle. Optionally, the cantilever may be scanned in three dimensions such that the cantilever vibrations produce a three-dimensional image of at least a portion of the sample.

BRIEF DESCRIPTION OF THE DRAWINGS

The embodiments herein will be better understood from the following detailed description with reference to the drawings, in which:

FIG. 3A is a schematic illustration depicting a probe in accordance with an exemplary embodiment of the present invention.

FIG. 3B is a schematic side view illustration of the embodiment of FIG. 3A.

FIG. 4 is a three-quarters schematic view of a modified probe in accordance with an exemplary embodiment of the present invention.

FIG. 5A is a schematic illustration of a modified probe in accordance with another exemplary embodiment of the present invention.

FIG. 5B is a schematic side view illustration of the embodiment of FIG. 3A.

DETAILED DESCRIPTION OF PREFERRED EMBODIMENTS

Figure 1:
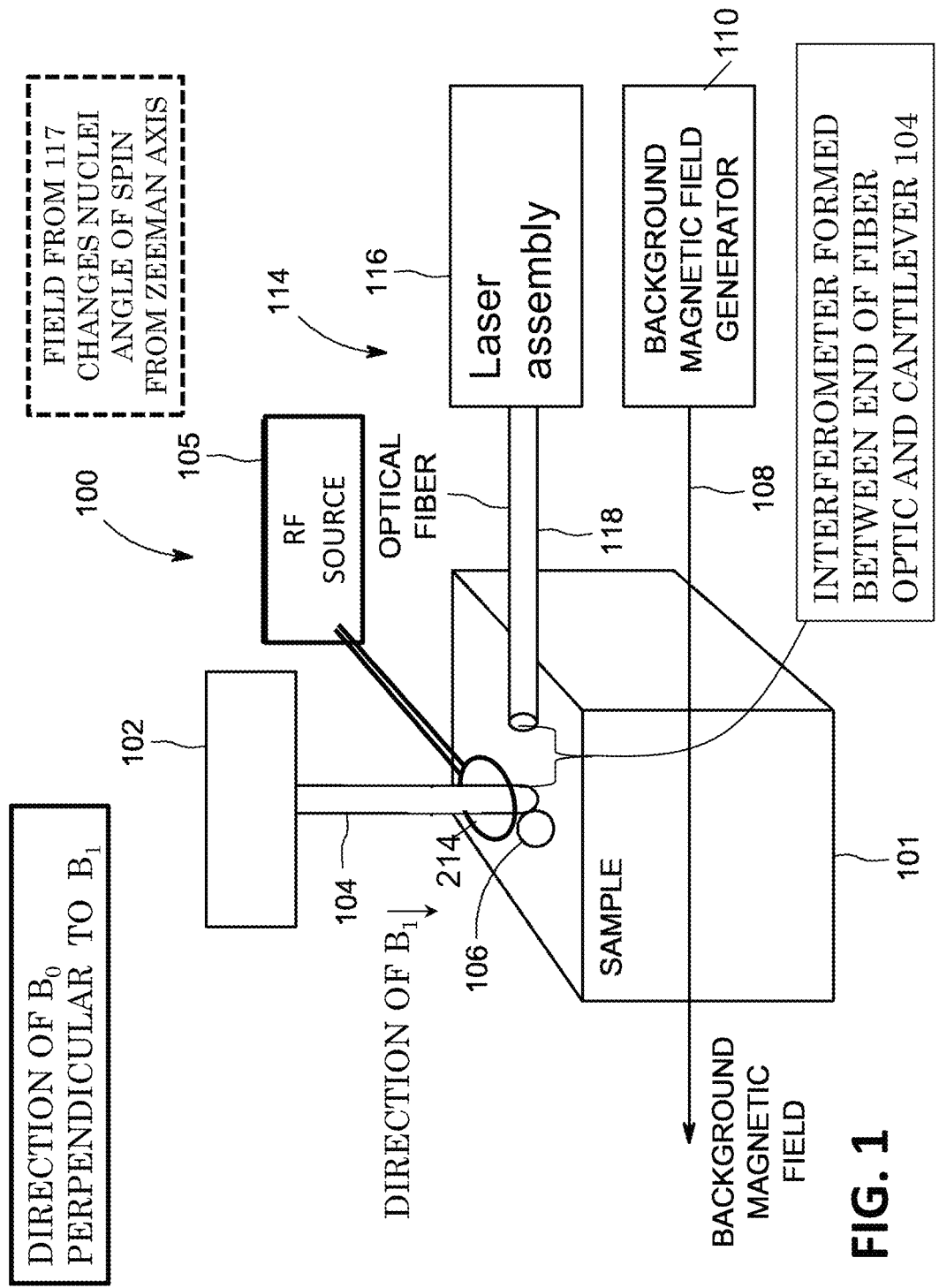
FIG. 1 is a schematic illustration of a preferred embodiment MRFM system in accordance with an exemplary embodiment of the present invention.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments of the invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the embodiments of the invention. The examples used herein are intended merely to facilitate an understanding of ways in which the embodiments of the invention may be practiced and to further enable those of skilled in the art to practice the embodiments of the invention. Accordingly, the examples should not be construed as limiting the scope of the embodiments of the invention.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element such as an object, layer, region or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It will be understood that, although the terms first, second, etc. may be used herein to describe various elements, components, regions, layers and/or sections, these elements, components, regions, layers and/or sections should not be limited by these terms. For example, when referring first and second conductors, these terms are only used to distinguish one conductor from another conductor. Thus, a first element, component, region, layer or section discussed below could be termed a second element, component, region, layer or section without departing from the teachings of the present invention.

Furthermore, relative terms, such as "lower" or "bottom" and "upper" or "top," may be used herein to describe one element's relationship to other elements as illustrated in the Figures. It will be understood that relative terms are intended to encompass different orientations of the device in addition to the orientation depicted in the Figures. For example, if the device in the Figures is turned over, elements described as being on the "lower" side of other elements would then be oriented on "upper" sides of the other elements. The exemplary term "lower", can therefore, encompass both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below. Furthermore, the term "outer" may be used to refer to a surface and/or layer that is farthest away from a substrate.

Embodiments of the present invention are described herein with reference to cross-section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. For example, a region or object illustrated as a rectangular will, typically, have tapered, rounded or curved features. Thus, the regions illustrated in the figures are schematic in nature and their shapes are not intended to illustrate the precise shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It will also be appreciated by those of skill in the art that references to a structure or feature that is disposed "adjacent" another feature may have portions that overlap or underlie the adjacent feature.

By way of background three magnetic fields are mentioned in the following description. The first being the background field $B_0$ that is used so that the spin direction of the sample nuclei are aligned and figuratively pointed up. The second magnetic field, $B_1$, is produced by the RF field transferred into at least one conductors from an RF source. This second field is used to change and/or control the angle or orientation of spin of the nuclei of the sample. The conductor transmits a radio frequency magnetic field that influences the nuclei in the sample. When the nuclei are influenced, they change the direction of their spin. The change in the angle of spin is generally measured from the Zeeman axis, the direction of $B_0$ defines the Zeeman axis, and provides information such as, for example, the composition of the sample. The third magnetic field is developed at the magnetic particle (106), which is influenced by the change in the angle of spin of the nuclei and which in turn influences the movement of the magnetic particle and hence its support, which may be, for example, a cantilever 104. The motion of the cantilever may be detected, for example, by the reflection of a laser beam (by reflector 318) transmitted, for example, through a fiber optic cable (118) using, for example, an interferometer effect.

This invention describes the case of a magnet tipped support, as shown in FIGS. 1, 3A, 4, 5, 6, 7, and 8, which may be, for example, a cantilever. The sample and cantilever system is immersed in a large background magnetic field, typically several Tesla, which acts to align the sample's magnetic moments parallel to the background magnetic field, $B_0$. This magnetic field may be produced, for example, by a magnetic field generator 110, as shown in FIG. 1. The attraction between the magnetic moments in the sample to the magnetic particle on the cantilever 104 acts on (or displaces) the magnetic particle, which in turn acts on (or displaces) the cantilever. This action or displacement of the cantilever is typically measured with a fiber-based optical interferometer capable of picometer displacement sensitivity. The technology used to make magnetic resonance force microscopy (MRFM) possible included magnetic resonance. Using the techniques of magnetic resonance, a RF pulse sequence is applied to the sample. This RF pulse acts to rotate the sample's magnetic moment and, depending on the pulse length and strength, it is possible to reverse the direction of the magnetic moments in the sample. As the magnetic moments in the sample are rotated (as a result of the RF source), the action on the cantilever also changes. Using MRFM, it is possible to perform magnetic resonance imaging (MRI) at the nanoscale, i.e., nanoMRI. The rapid decrease in the cantilever-mounted particle's magnetic field, measured as a function of distance from the magnetic particle, results in a magnetic field gradient across the sample. Because the frequency of the RF pulse must be commensurate with the total magnetic field (background field $B_0$ plus the magnetic field from the particle on the cantilever) experienced by the sample's nuclear magnetic moment (spin), it is possible to select the spatial slice through the sample where spins are reversed. The selected spatial slice is referred to as the sensitive slice or the resonant slice in the sample. The spins of the sample are in resonance with the RF field in the slice or resonant region. The force and/or force-gradient on the magnetic particle created by the rotating sample spins is detected by monitoring the position of cantilever 104 with a laser interferometer as shown, for example, in FIG. 3. Relying on a magnetic field gradient and using imaging techniques, a spin density map of the sample is produced. Three dimensional images may be produced by moving the sample and magnetic particle in three-dimensions with respect to each other, so as to construct a three-dimensional (3-D) image of the sample's spin (magnetic moment) density, hence nano-MRI is achieved.

Setups for mechanically detected spin resonance include positioning the sample on cantilever with the magnet separately supported and positioning the magnet on cantilever with the sample separately supported. Alternative methods of performing the latter include placing the sample on the RF source. One set-up is placement of the sample on an RF strip line.

A preferred embodiment of the present invention comprises a magnet on cantilever with the sample being in close proximity to an RF source. The principal advantages include: 1) the sample is not restricted in size or mass; 2) the sample does not need to be placed on the cantilever, reducing the sample prep required; 3) The sample does not need to be placed on a strip line, so the sample prep required is reduced; 4) the RF source and cantilever are coaxial, permitting access to the entire sample and not limiting access to the sample edge.

A preferred embodiment of the present invention comprises a Scanning Probe Magnetic Resonance Force Microscope (SPMRFM) that has not been used previously with an MRFM system. The design has numerous advantages and improvements over prior art, including: 1) the capability of scanning over an arbitrary sample size and geometry, restricted only by the scanning range of the sample holder; 2) providing a larger $B_1$ field to RF power ratio; 3) permitting low RF power Adiabatic Rapid Passage (ARP) sweeps for the necessary $B_1$, which will lower the thermal load on the system during data acquisition; and 4) providing short duration or "hard" Pi pulses, desired for NMR spectroscopy measurements. The improvements over previous techniques include: 1) surface mounting the RF coils provides a rigid mechanical base which serves to protect the coils from damage, since the coils are intended to scan over a sample surface with a gap, for example, on the order of 100 microns or less; 2) the RF coils may be fabricated on a substrate (as shown, for example, in FIG. 8, that provides a non-radiative dependent heat conduction path out of the probe body); 3) use of surface or substrate mounted RF coils facilitates production so as to provide reliability, repeatability and precise configurability in their design; 4) the number of coils, their spacing and size can all be controlled and tailored for specific RF performance characteristics. Specifically, the density of the coil, for example, the conductors may be formed using 10 micron diameter traces with a 10 micron space between the traces, which permits a much higher $B_1$ to current ratio than obtained with previous techniques. Other dimensions may be utilized dependent upon the application and size requirements.

Embodiments of the present invention comprise a probe for use in magnetic resonance force microscopy (MRFM). Embodiments of the probe may be used in an MRFM technique known as Springiness Preservation by Aligning Magnetization (SPAM). See for example, "Observation of Real Time Magnetization Inversion-recovery Using the SPAM Geometry and the CERMIT Protocol," by Dimitri A. Alexson and Doran D. Smith, ARL-TR-5742, U.S. Army Research Laboratory, September 2011 (hereby incorporated by reference).

Referring again to FIG. 1, the four main elements of the probe head are a cantilever 104 with a magnetic particle 106 attached to its free end, optical fiber, RF coil 214, and sample 101 which may be mounted on a sample stage. The optical fiber 118, 310 (FIG. 3) is used to sense the position of the cantilever. The RF coil is used to generate an RF magnetic field $B_1$ which excites the nuclei in the sample. The sample stage may be moved approximately 5 mm in each of three dimensions to position the sample relative to the cantilever 104, which may be for example, a silicon cantilever 450 microns long, 5 microns wide, and 300 nm thick. The cantilever 104 may include a 30 micron diameter optical reflection pad (318) centered 70 microns from the free end of the cantilever. Attached to the free end of the cantilever and overhanging it is a 6 micron diameter Ni particle. Several Tesla magnetic field may be used to fully magnetize the Ni particle. The cantilever's amplitude may be controlled by a piezoelectric stack that vibrates the base of the cantilever. This allows the use of the CERMIT protocol (see for example, "Observation of Real Time Magnetization Inversion-recovery Using the SPAM Geometry and the CERMIT Protocol," by Dimitri A. Alexson and Doran D. Smith. ARL-TR-5742, U.S. Army Research Laboratory, September 2011) which relates the change in the cantilever's frequency to a change in the magnitude of the net magnetization along the Zeeman axis.

By adopting the SPAM geometry and using the concepts of the present invention, accurate scanning of arbitrarily sized samples is achieved, not limited to scanning the edges of a sample.

Figure 2:
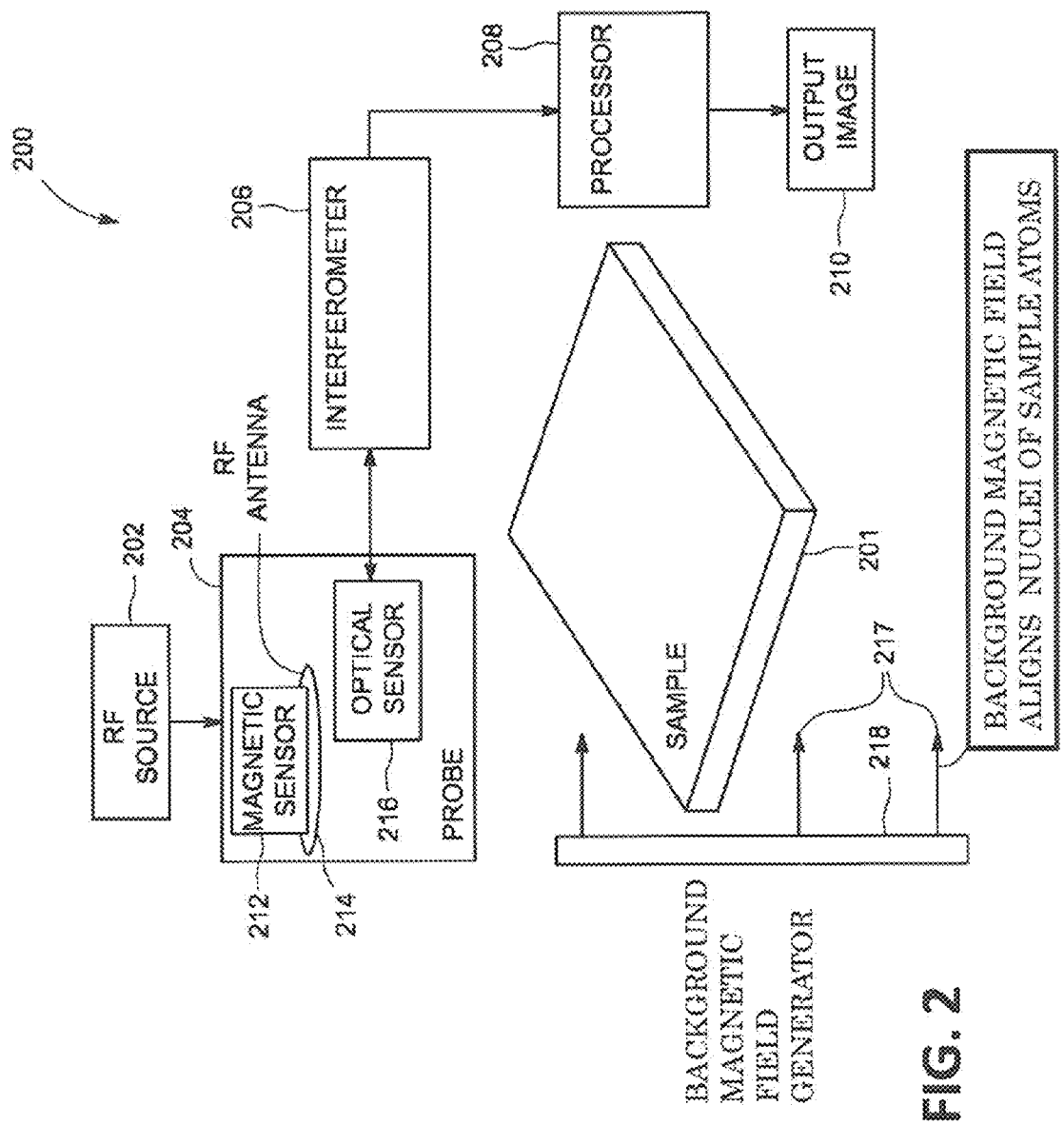
FIG. 2 depicts a block diagram of an MRFM system in accordance with an exemplary embodiment of the present invention.

FIG. 2 depicts a block diagram of an MRFM system 200 in accordance with an exemplary embodiment of the present invention. The system 200 generally has an RF source 202 coupled to a probe 204. The probe 204 is coupled to an interferometer 206 for performing optical measurements using the optical sensor 216 in the probe 204 of sample 201. The interferometer 206 transmits the measurements to a processor 208. The processor 208 generates an output image 210 based on the measurements or oscillations of portions of the probe 204. The probe 204 comprises a magnetic sensor 212, an RF antenna 214 and an optical sensor 216. The apparatus 200 is kept in a background magnetic field 217 (approximately 9 Tesla) generated by a background magnetic field generator 218. In an exemplary embodiment, the background magnetic field generator 218 comprises two one inch diameter Samarium Cobalt (SmCo) magnets, which can be used for ESR; while for NMR, a superconducting magnet is used. In an exemplary embodiment, the magnetic sensor 212 is comprised of a cantilever coupled with a smaller SmCo particle (for example, 10 μm in diameter) which generates a spatially inhomogeneous field. The magnetic field experienced at a particular point in the sample 201 is the sum of the background magnetic field and the magnetic field generated by the magnetic sensor 212. The RF antenna 214 at least partially surrounds the magnetic sensor 212. The RF antenna 214 generates an RF magnetic field which causes the spin in the particles of the sample 201 to reverse and oppose the SmCo particle on the bridge of the magnetic sensor 212. This repeated reversal of the spin of the particles in sample 201 causes the magnetic sensor 212 to oscillate at a particular frequency. The interferometer 206 senses oscillation of the magnetic sensor 212 using optical sensor 216 by using optical fiber 217 to reflect a laser off of the magnetic sensor 212. In another exemplary embodiment, the sample 201 is directly coupled to the bridge comprising the magnetic sensor 212 and a magnetic particle array of SmCo particles is proximate the magnetic sensor 212. According to an exemplary embodiment, the optical fiber 118 is 125 microns in diameter and is within approximately 1/10 of a millimeter of the magnetic sensor 212. In an exemplary embodiment, the optical sensor 216 is an optical fiber approximately twenty five times greater in diameter than the width of the bridge of the magnetic sensor 212. The gap between the optical fiber and the magnetic sensor 212 is fixed at a particular distance in this embodiment.

FIG. 3A is an illustration depicting a probe 300 in accordance with an exemplary embodiment of the present invention. The probe 300 comprises an RF antenna 302, which may be formed as a circular wire surrounding a magnetic sensor 305, or any conductor circuit having a path or trace that provides a magnetic field. The magnetic sensor 105 comprises an oscillating or support element 304 having a magnetic particle 306 at its end. The oscillating or support element 304 may be a bridge, cantilever, or other structure that resonates. A cantilever is shown with, in an exemplary embodiment, an approximately 100 μN/m (micro-Newtons per meter) spring constant, a mechanical Q of about 10,000-100,000 and a resonance frequency of about 1000 Hz. In this exemplary embodiment, the cantilever is made of silicon using a micro-electromechanical systems (MEMS) fabrication process. The RF antenna 302 is positioned above sample 201 (shown in FIG. 2), by, for example, a distance of 1 to 100 μm. Above the sample, the optical sensor 310 emits light onto the oscillating element 304, which oscillates in the field perpendicular to the background magnetic field 317, generated by the background magnetic field generator 218 shown in FIG. 2. The RF antenna 302 creates an RF signal that permeates the sample 201 (shown in FIG. 2), altering the spin of particles in the sample 201. The spin changes alternatively oppose and attract the particle 306 causing the magnetic sensor 305 to resonate by displacing the oscillating element 304 and/or the spin changes produce a change in the force gradient experienced by the particle 306 and cause the magnetic sensor 305 to change the resonant frequency of the driven oscillating element 304. In an exemplary embodiment, the RF antenna 302 generates an RF signal of 50 MHz to 380 MHz. The displacement of the oscillating element 304 is measured by the optical sensor 310. The sample 201 is positionable with respect to the alignments of the RF antenna 102, the oscillating element 304 and the optical fiber 310, by the use of a sample stage 312, as described in commonly assigned U.S. patent application Ser. No. 13/361,223 entitled "APPARATUS FOR PERFORMING MAGNETIC RESONANCE FORCE MICROSCOPY ON LARGE AREA SAMPLES" file Jan. 30, 2012, hereby incorporated by reference. The RF antenna 302, the support 301 for the oscillating element 304 and the optical fiber 310 may be positioned with respect to each other or may be movable relative to one another. The RF antenna 302 is closer to the sample 201 than it would be in otherwise different geometries because it is not constrained to the edge of the sample, causing a larger RF magnetic field to radiate through the sample 201.

The RF antenna 302 produces both RF magnetic field and RF electric fields. Typically, MRFM uses the RF magnetic field to oscillate the spin of atoms in the sample. The RF electric field is undesired in MRFM because it causes transients in the magnetic sensor 305 oscillation frequency for the oscillating element 304. The RF electric field along the center axis of an ideal loop antenna is zero. The support 301 for the oscillating element 304 and the magnetic particle 306 are then located in a much stronger RF magnetic field than in conventional MRFM systems. In an exemplary embodiment the RF antenna 302, the antenna has a nearly circular shape with a small gap at which the input lead 314 and the output lead 316 extend outwards on the same plane. In other embodiments, the leads 314 and 316 extend downward or in another direction. In yet another embodiment, the RF antenna 302 does not have extended leads, but receives RF power through an inductive coupling to another segment of nearby wire (not shown).

FIG. 4 is a three-quarters view of a modified probe 400 in accordance with an exemplary embodiment of the present invention. In exemplary embodiments, the RF antenna 402 is thicker than that shown in FIG. 3, and may not fit under the optical fiber 310 without touching the sample 201. In this embodiment, the RF antenna 402 is formed as a coil that is looped up and over (or bridges) the optical fiber 310 and the leads 414 and 416 lead to an RF source. The loop 403 causes a small distortion in the magnetic field created in the area of the sample directly underneath the antenna 402 and is accounted for during measurement processing.

FIG. 5A is a plan view illustration of a modified probe 500 in accordance with another exemplary embodiment of the present invention. In this geometry, the RF antenna 502, with leads 514 and 516, does not have a loop 403 as shown in FIG. 4, but the RF antenna 502 is also shown in a thicker embodiment where the optical fiber 310 will not fit underneath without touching the sample 201. Therefore, in this embodiment, the optical fiber 310 is raised above the RF antenna 502 (as shown in FIG. 5B), avoiding any distortions created in the magnetic field by using a non-uniform antenna structure. In another embodiment, the optical fiber 310 is in the plane of the antenna, located between the leads 314 and 316.

Figure 6:
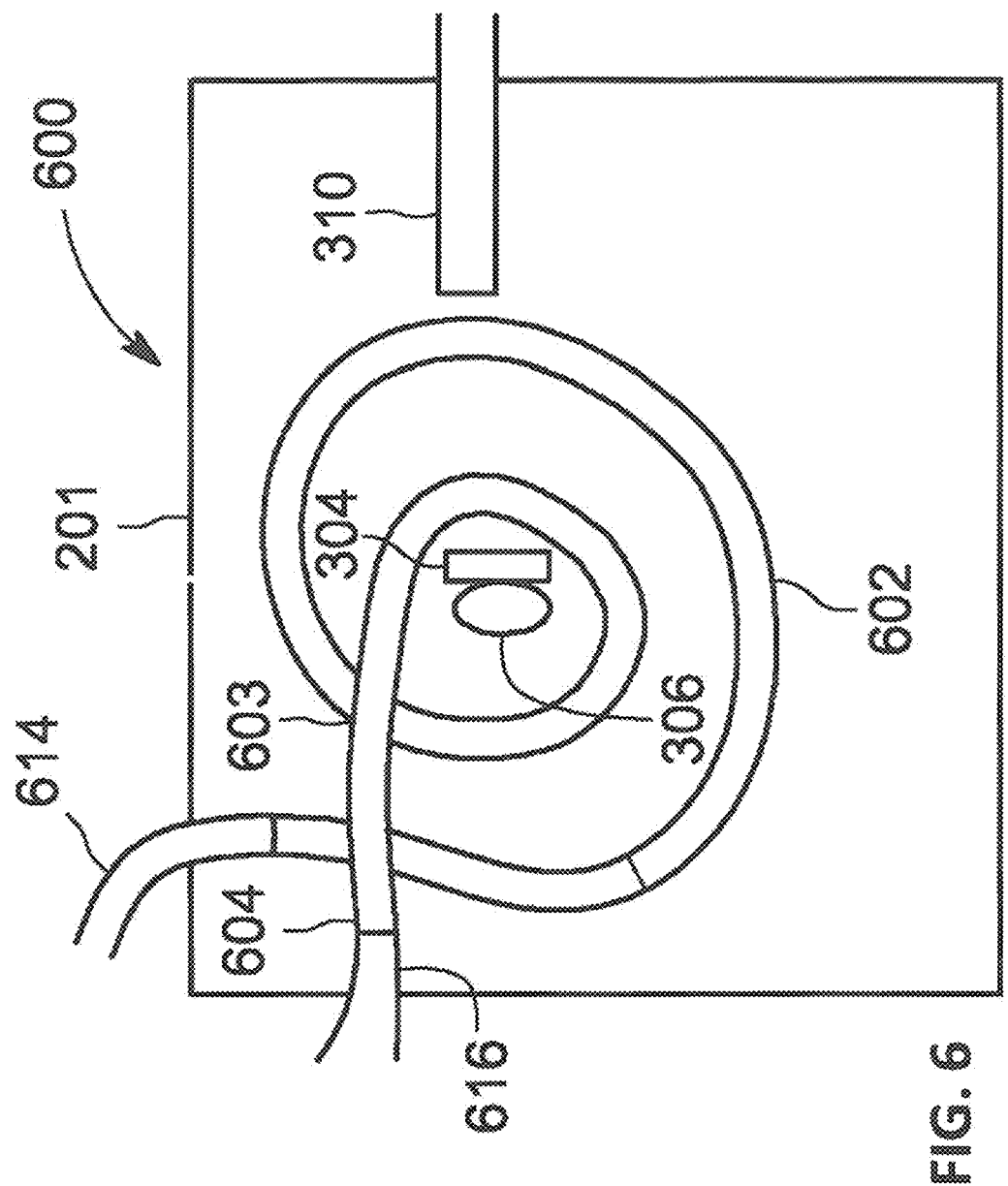
FIG. 6 is a top-down schematic illustration of a modified probe in accordance with another exemplary embodiment of the present invention.

FIG. 6 is a top-down illustration of a modified probe 600 in accordance with another exemplary embodiment of the present invention. In this embodiment, RF antenna 602, with leads 614 and 616, is coiled over itself and around the magnetic sensor 305 (not shown in FIG. 6). In an exemplary embodiment, the upper coil of RF antenna 602 is raised at section 603 above the lower coil of RF antenna 602 and lowered at section 604. In other embodiments, one portion of the RF antenna 602 is lowered at section 603 underneath the other portion and raised again at section 604. The coiling of RF antenna 602 (e.g., using more than one turn of the coil) increases the magnetic field in the sample 201 and allows for better inversion of spin of the particles in the sample 201. The coiling of RF antenna 602 results in a more accurate MRFM image of the structure of the sample 201. Optionally, the fiber 310 can be located above, below or between the coils.

Figure 7:
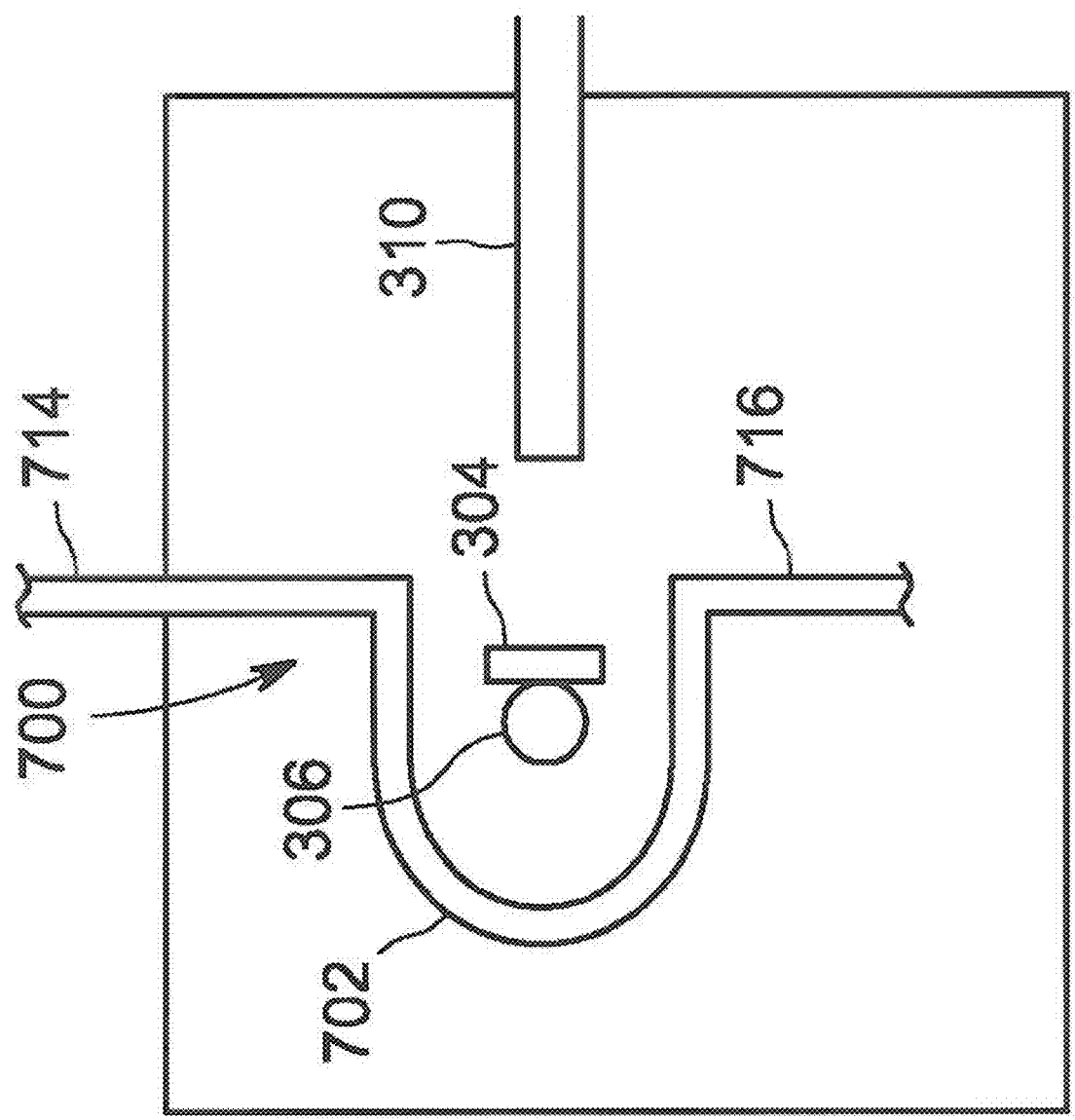
FIG. 7 is a top-down schematic illustration of a modified probe in accordance with another exemplary embodiment of the present invention.

FIG. 7 is a top-down illustration of a modified probe 700 in accordance with another exemplary embodiment of the present invention. Sample 201 is placed below RF antenna 702, with leads 714 and 716, where the oscillating element 304 tipped with a magnetic particle 306 is placed in the RF magnetic field of the RF antenna 702 and the optical fiber 310 detects small displacements in the oscillating element 304. In this embodiment, the RF antenna 702 is in a horseshoe shape. In this configuration, the optical fiber is avoided completely due to the shape of the antenna. The RF antenna 702 also avoids the problem of creating a distorted magnetic field in the sample 201 by doubling over itself or creating a loop over the optical fiber 310 as in other geometries.

Multiple Conductor Embodiments

Figure 8:
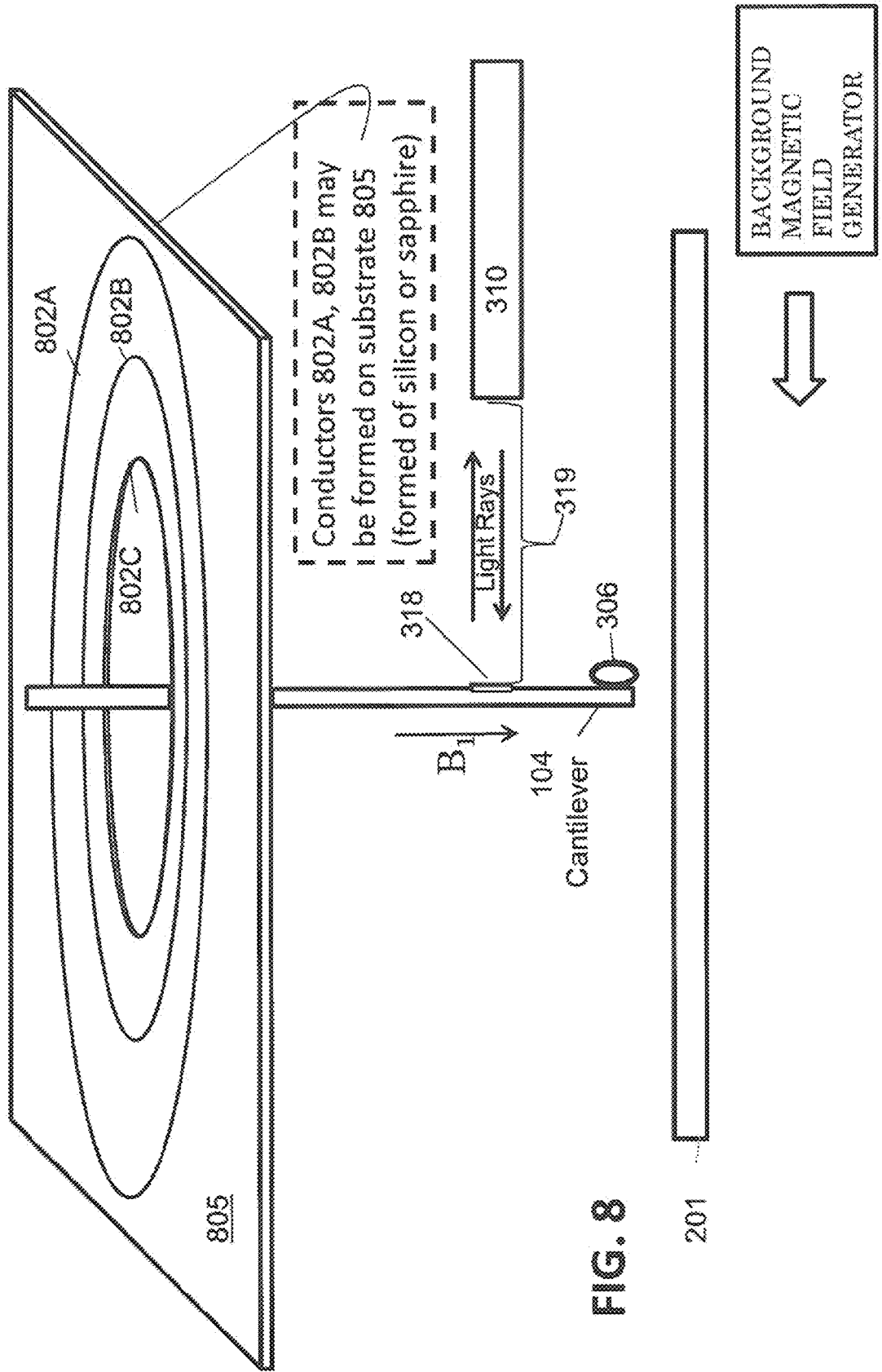
FIG. 8 is a schematic illustration of a preferred embodiment comprising multiple conductors 802A, 802B. In the illustrated Scanning Probe MRFM (SPMRFM) setup, the $B_1$ of the RF source is aligned with the long axis of the cantilever. The direction of $B_o$ with respect to $B_1$, not shown in the figure, is always perpendicular to $B_1$. The relative orientations of the magnet tipped cantilever, RF source, optical fiber and sample are shown.

Another preferred embodiment of the present invention provides an RF source that is coaxial with the mechanical detector, the magnet tipped cantilever, as represented in FIG. 8. FIG. 8 is a schematic illustration of a preferred embodiment comprising multiple conductors 802A, 802B. The terminology "multiple conductors" as used herein is intended to encompass, but is not limited to, multiple coils or loops. The multiple loops or coils need not be planar, and may be for example, multiple loops or coils of a spiral conductor. Although the conductors 802A, 802B, appear as loops, the conductors may be of any shape such as, for example, polygonal or may be of an irregular shape such as that depicted in FIG. 6. In the Scanning Probe MRFM (SPMRFM) setup of FIG. 8, the $B_1$ of the RF source is aligned with the long axis of the cantilever. The direction of Bo with respect to $B_1$, not shown in the figure, is always perpendicular to $B_1$. The relative orientations of the magnet tipped cantilever, RF source, optical fiber and sample are shown.

The conductors of FIG. 8 are depicted on a substrate having an internal hole 802C. Fabricating the conductors 802A, 802B on a substrate provides a rigid mechanical base which serves to protect the coils from damage, since the coils are intended to scan over a sample surface with a gap, for example, on the order of 100 microns or less. Fabrication on a substrate provides a non-radiative dependent heat conduction path out of the probe body, and the use of surface or substrate mounted RF coils facilitates production so as to provide reliability, repeatability and precise configurability in their design. The number of coils, their spacing and size can all be controlled and tailored for specific RF performance characteristics. Specifically, the density of the coil, for example, the conductors may be formed using 10 micron diameter traces with a 10 micron space between the traces, permits a much higher $B_1$ to current ratio than obtained with previous techniques. Although the RF connections to a RF signal generator are not shown in FIG. 8, connections such as those illustrated in FIGS. 10 and 11 may be utilized.

As depicted in FIG. 8, an interferometer is formed between the fiber optic 310 and the reflector 318 of the cantilever 104. The components of FIGS. 1, 2 and 3 may be used in the embodiment of FIG. 8 and are hereby incorporated by reference. Note that the antenna 214 of FIGS. 1 and 2, and 302 of FIG. 3 may comprise multiple loops as shown in FIGS. 8, 9A, 10, 11, and 12. By the reflection of a laser beam (by reflector 318) transmitted, for example, through a fiber optic cable (310), an interferometer effect is achieved.

Figure 9A:
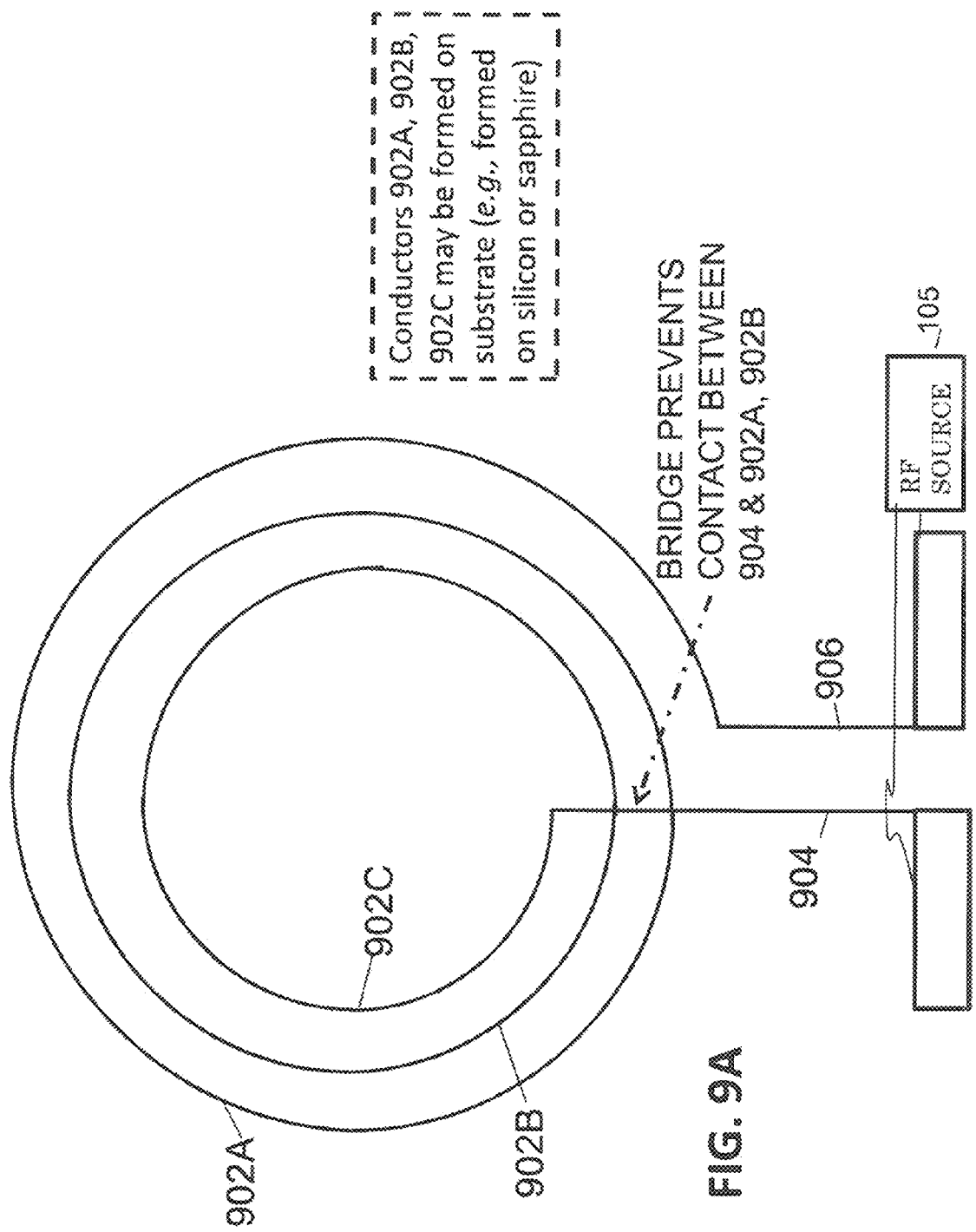
FIG. 9A is a drawing of surface coils in spiral geometry using a bridge to connect to the inner coil.
Figure 9B:
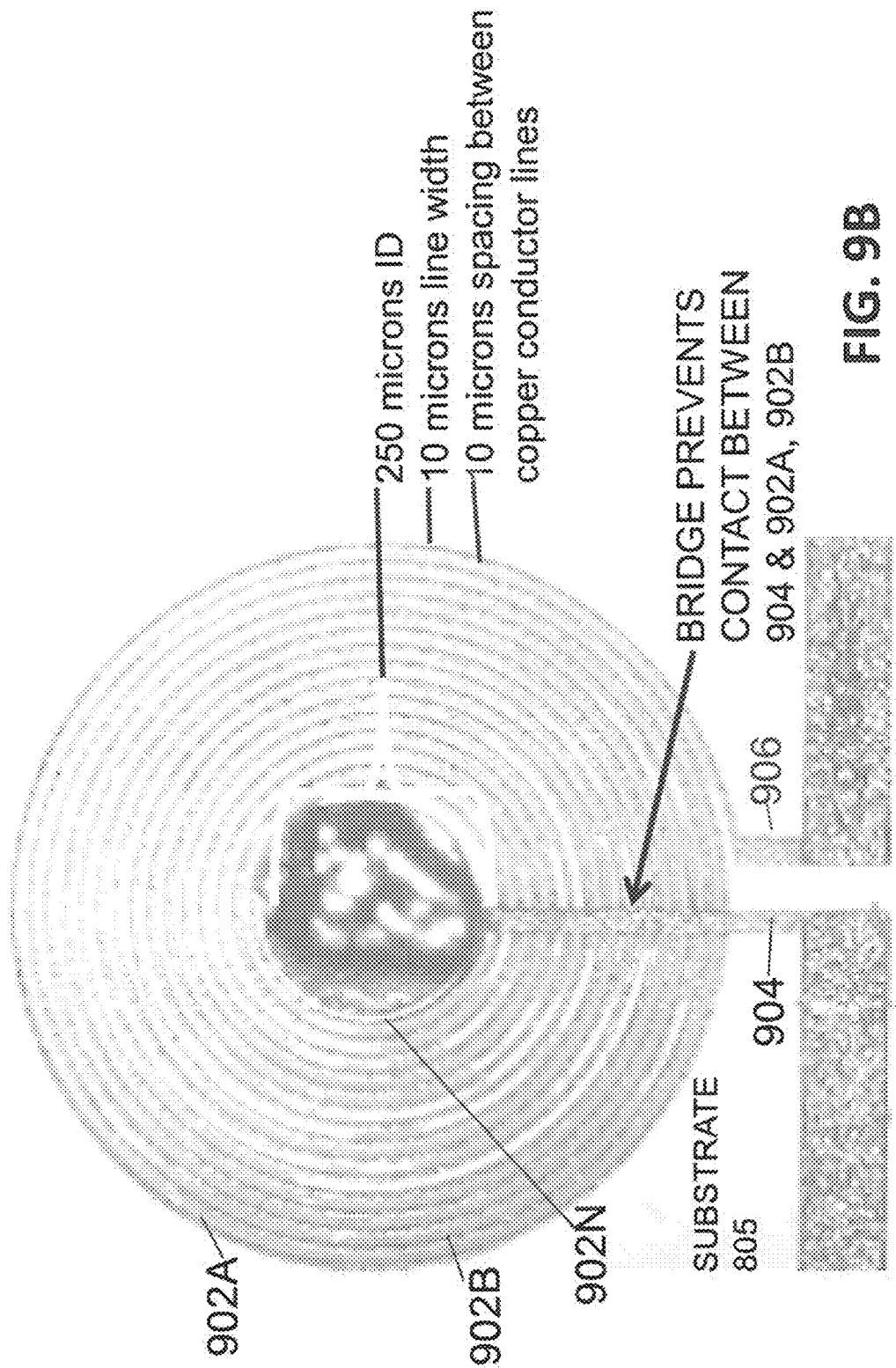
FIG. 9B is a photograph of a spiral Cu coil on a silicon wafer with an etched hole in the center for cantilever access. A bridge connects the inside of the spiral with the outside end. The ends extend to larger Cu pads that can be electrically connected to for RF delivery.
Figure 10:
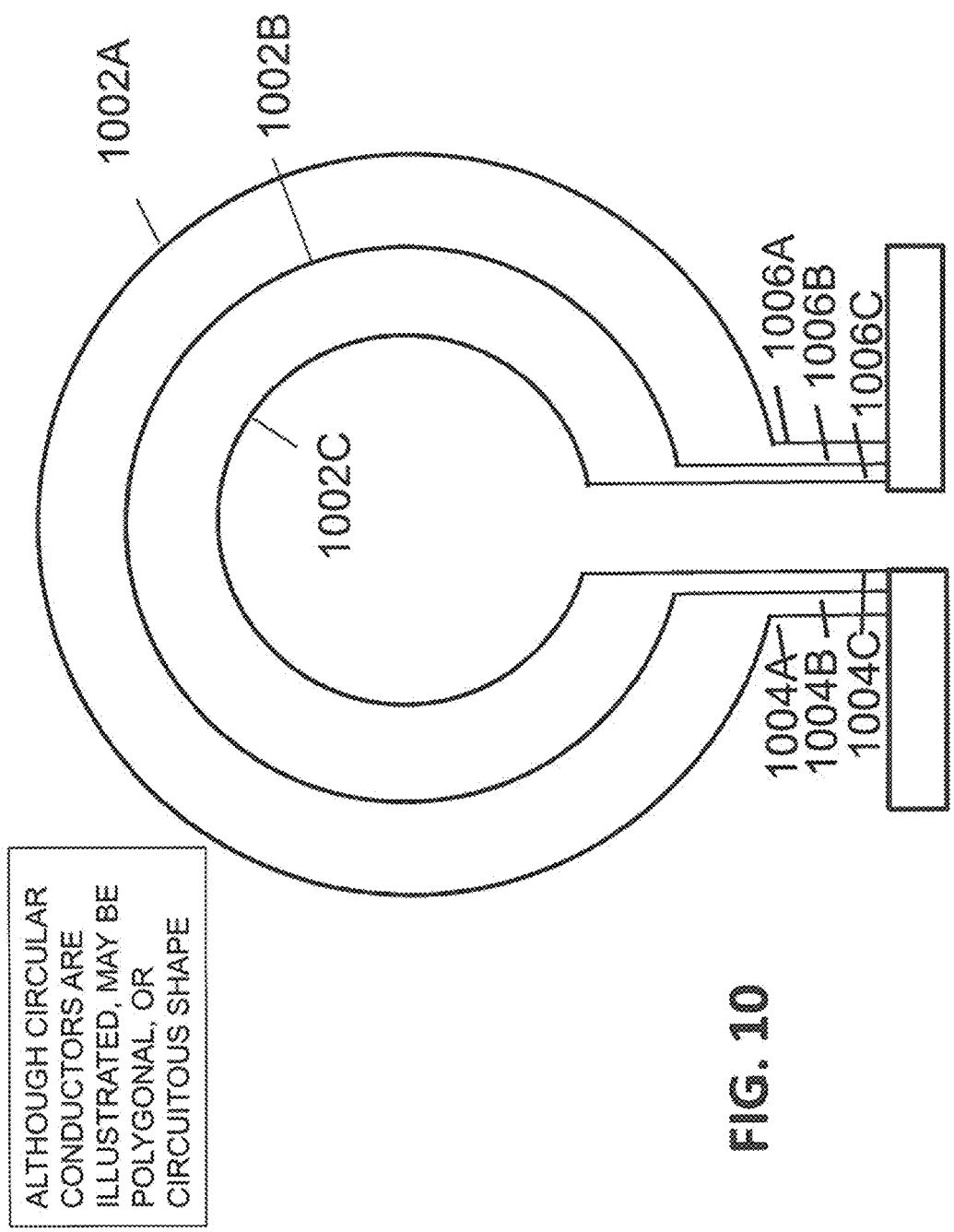
FIG. 10 is a drawing of surface coils in a nested geometry. All the coils are electrically connected.
Figure 11:
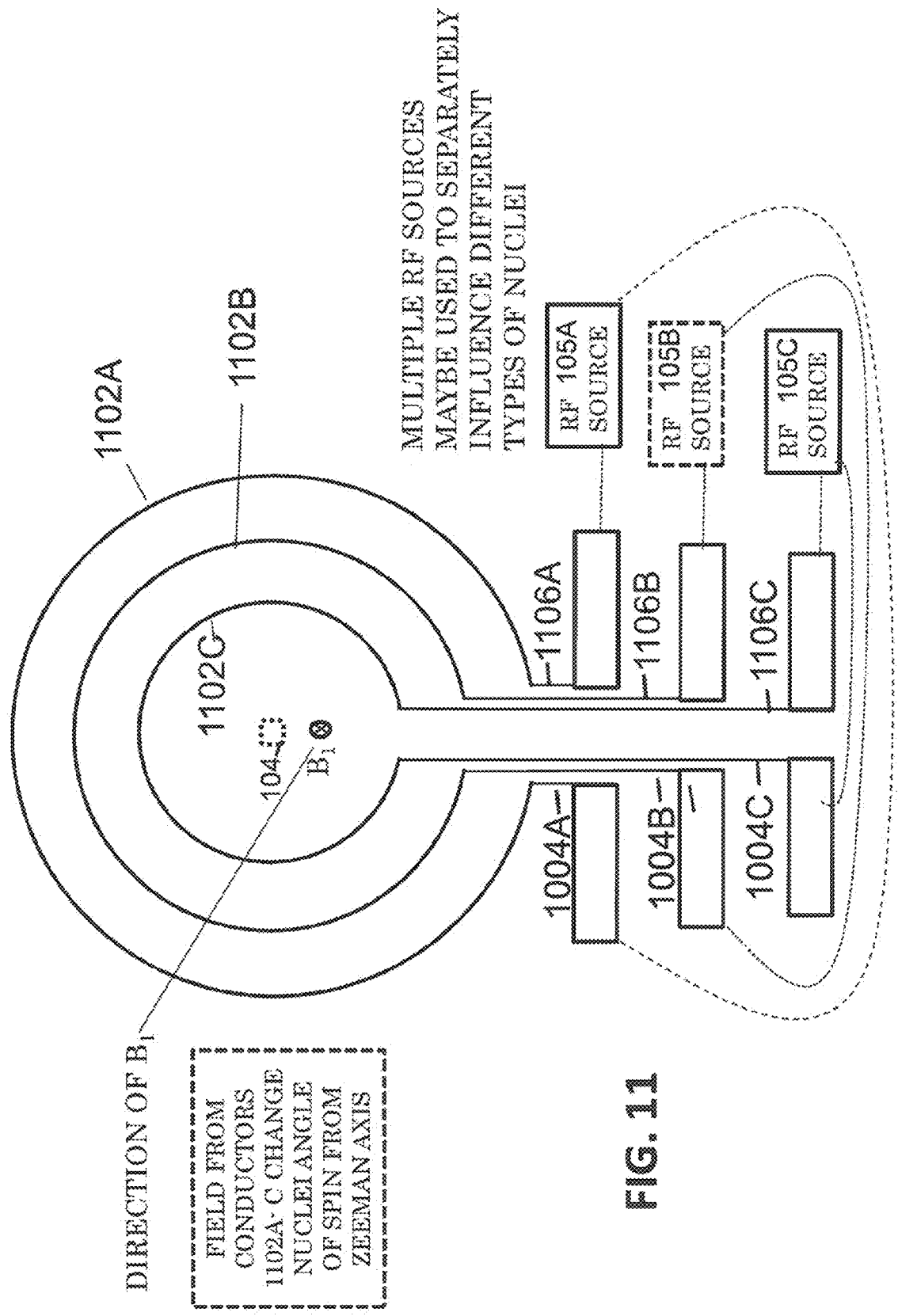
FIG. 11 is a drawing of surface coils in a nested geometry which are individually addressable.
Figure 12:
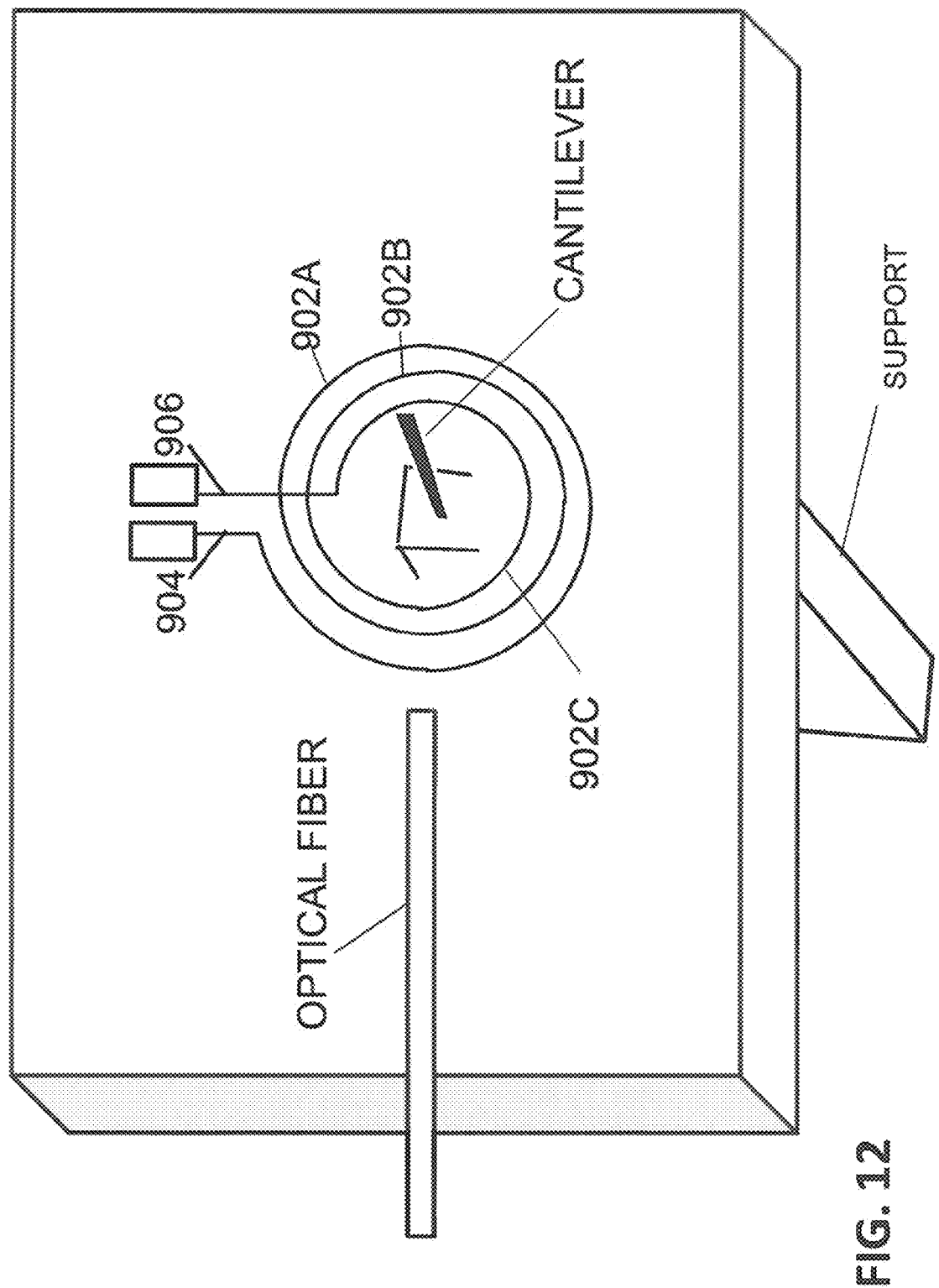
FIG. 12 is a perspective drawing showing the relative positions of the RF chip, cantilever chip and optical sensing fiber. The surface mounted coils are represented in the drawing by a spiral.
Figure 13:
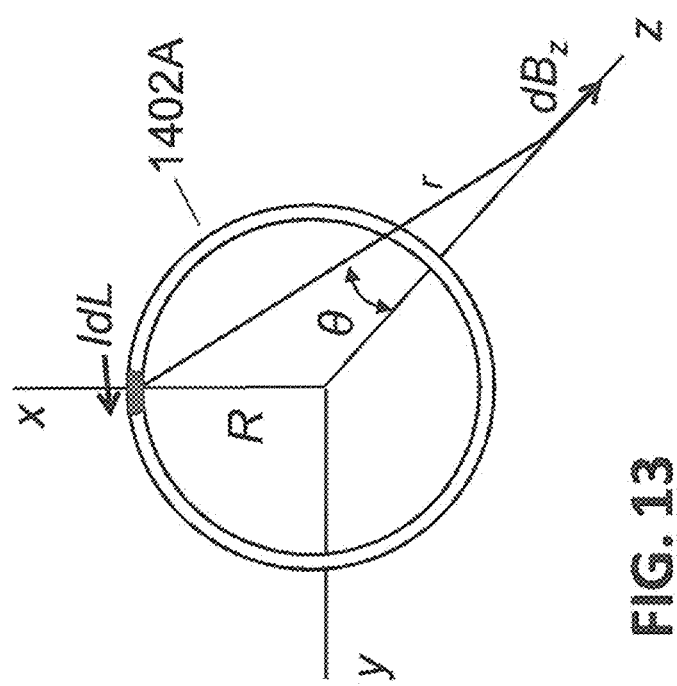
FIG. 13 is a drawing of a wire conductor or loop element lying in the xy plane. The magnetic field due to the loop along the axis perpendicular to the plane of the loop centered at its origin is shown. The optimal loop radius to maximize $B_1$ when the distance z is held constant is given by the product of the distance $z*\sqrt{2}$.

A three dimensional representation of the RF chip and cantilever chip is shown in FIG. 12. This combination can be scanned over a sample surface of arbitrary size and shape. The RF source is required for the manipulation of a sample's magnetic moments, arising from either nuclei or electrons. The sample's magnetic moments are manipulated for many reasons. Primary among these is to measure the magnitude of the spin's magnetization along the Zeeman axis, the Zeeman axis being defined by the direction of the background magnetic field $B_0$ and to deliver RF pulses to the sample's spins for Nuclear Magnetic Resonance (NMR), Electron Spin Resonance (ESR) and Magnetic Resonance Imaging (MRI) techniques. Spiral and nested planar coil geometries are shown in FIGS. 9, 10 and 11. A photograph of planar Cu spiral traces on silicon with a hole etched in the center to allow the cantilever to pass through is shown in FIG. 9B.

Figure 15:
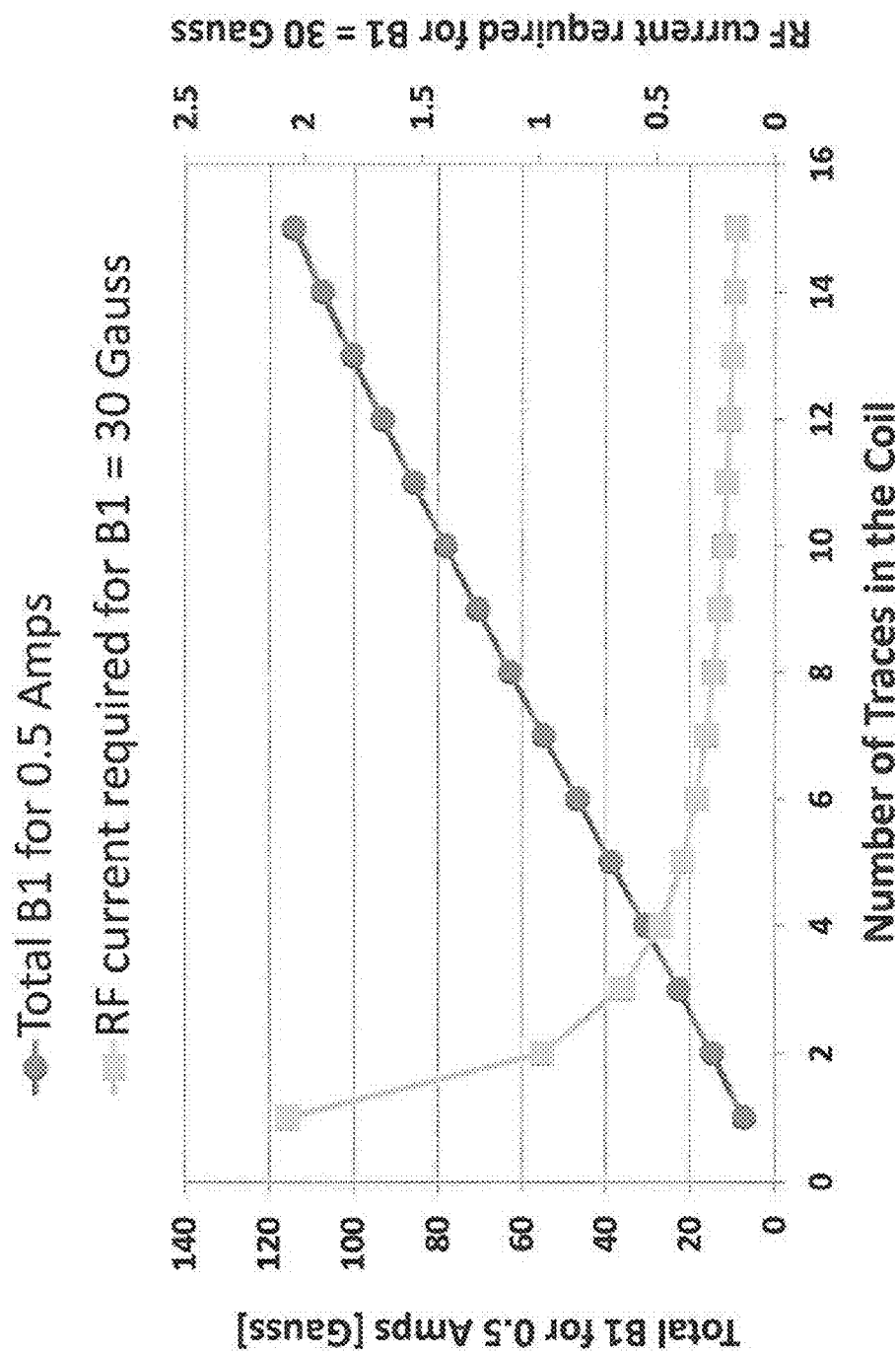
FIG. 15 is a graph displaying the magnetic field value as a function of number of loop elements for a fixed distance and loop current. Also displayed is the current required to produce a $B_1$ of 35 Gauss as a function of number of turns.
Figure 16:
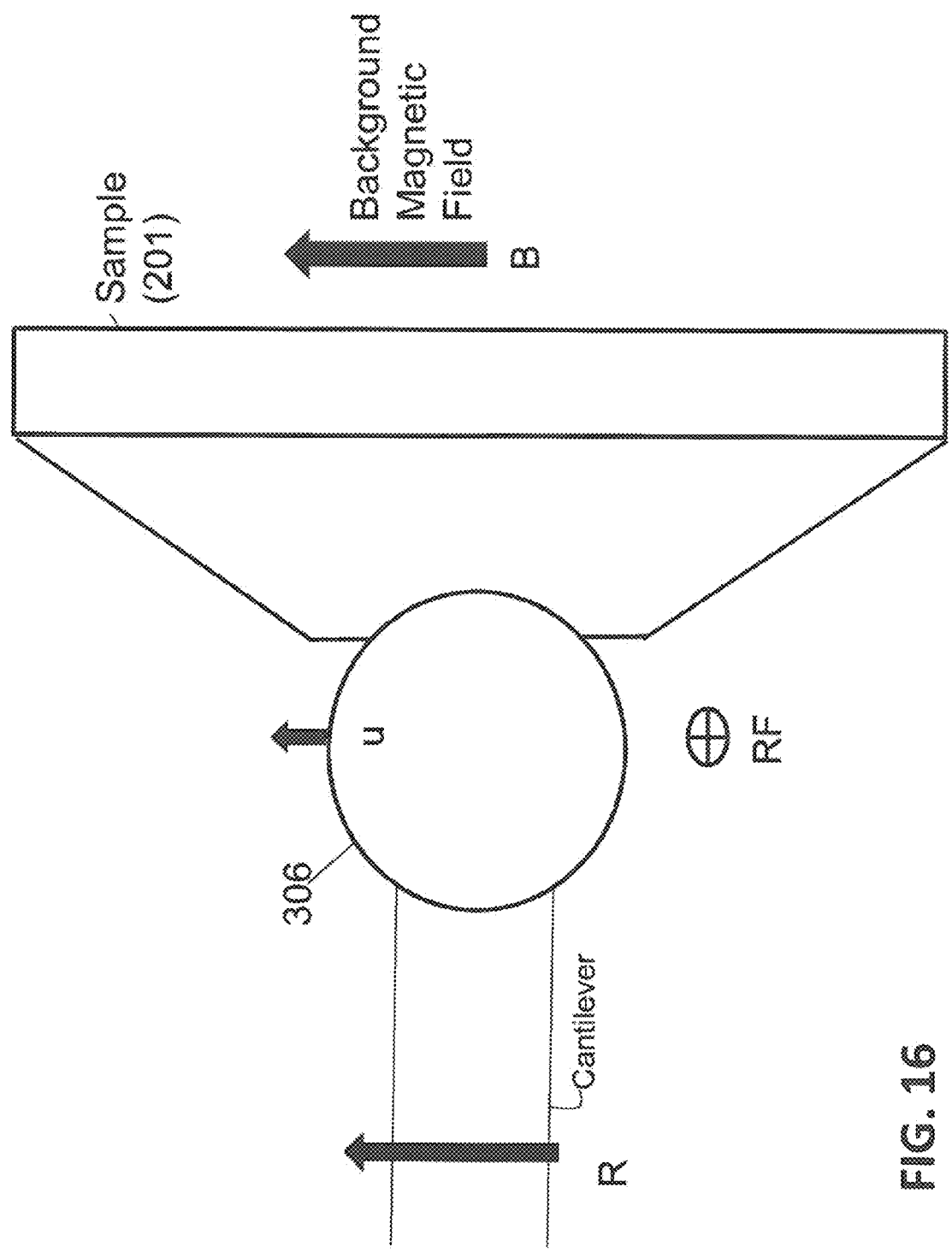
FIG. 16 is a force field diagram including the background magnetic field $B_0$. R is the rotation axis of the cantilever with the attached magnetic particle, RF is the direction of the RF magnetic field.

To measure the magnitude of the spin's magnetization along the Zeeman axis with MRFM, a multitude of techniques are employed. The common trait among many of these techniques is the use of an Adiabatic Rapid Passage (ARP) RF sweep delivered by the RF source. The spins in the sample are cyclically inverted by the ARP sweep and the periodic inversion of the sample's spins causes an action on the cantilever which is measured in either amplitude or frequency changes of the cantilever depending on the detection protocol in use. The RF source must create a $B_1$ field larger than the internal local magnetic field in the sample that is seen by the spins, so that the sample's spins can be inverted by the ARP RF sweep. In the case of the magnet tipped cantilever, the sample's spins act on the magnet on the cantilever. In the case of the sample tipped cantilever, the tip of the cantilever with the sample is brought to close proximity of a magnet. In either case, the magnetic moment of the magnet is fixed and the sample's spins are cyclically inverted. For an amplitude detection protocol the cyclical inversion must be done for a period of time long enough for the cantilever to build a detectable oscillation amplitude. During the time that the RF is on, the sample and probe head become heated by the RF source. The $B_1$ due to each loop (trace) element adds linearly, at any point in space, due to the rule of superposition in electromagnetics. Therefore, if the magnitude of $B_1$ is held constant, the ratio of $B_1$ created by the coil to RF power delivered to the coil increases with the addition of traces in the coil, up to a point. The resistive heating in the coil is a function of the total length of the coil and typically increases with the addition of more turns. The DC resistance of the coil wire is linear with its length. Thus, with the current invention it is possible to decrease the coil RF current requirements, without a significant penalty in coil heating, for a fixed $B_1$. The number of traces in the coil, their width and separation can be chosen for desired $B_1$, RF power, resistive heating, inductive and capacitive load performance requirements. For the example shown in FIG. 15, distance z held constant at 150 microns and the etched hole diameter used was 250 microns with a trace width and spacing of 5 and 10 microns, respectively for the conductor or loop elements.

Pulse sequences which are used with Nuclear Magnetic Resonance NMR, Electron Spin Resonance (ESR) and Magnetic Resonance Imaging (MRI techniques are often short duration or "hard" pulses. The resonance condition of an RF pulse is met, when the frequency of the RF pulse is resonant with a sample spin for a given background magnetic field $B_0$. A Pi pulse is defined as a pulse which inverts the sample's spins. The duration of a Pi pulse necessary is inversely proportional to the magnitude of $B_1$. Thus, the larger $B_1$ that can be produced by the RF source, the shorter duration pulse is required to invert the sample spins. Many pulse sequences and techniques used in NMR, ESR and MRI are directly compatible with MRFM. For the case of nuclear magnetic spins, the pulse duration can be near a microsecond for a large $B_1$. The preferred embodiment of the present invention has a further advantage over prior embodiments because the larger $B_1$ further decreases the thermal load on the sample and probe head because the RF Pi pulse is of shorter duration.

NMR spectroscopy requires a highly spatially homogeneous background magnetic field. MRFM by its nature introduces a large magnetic field gradient in the sample. For NMR spectroscopy to be performed using MRFM, the magnetic field gradient due to the magnetic particle must be temporarily removed. In the MRFM setup using a magnet tipped cantilever as shown in FIG. 8, one method to accomplish this is to shuttle the sample away from the magnet tipped cantilever. Another method is to temporarily move the magnet tipped cantilever away from the area of interest, while the RF encoding is done.

Figure 14:
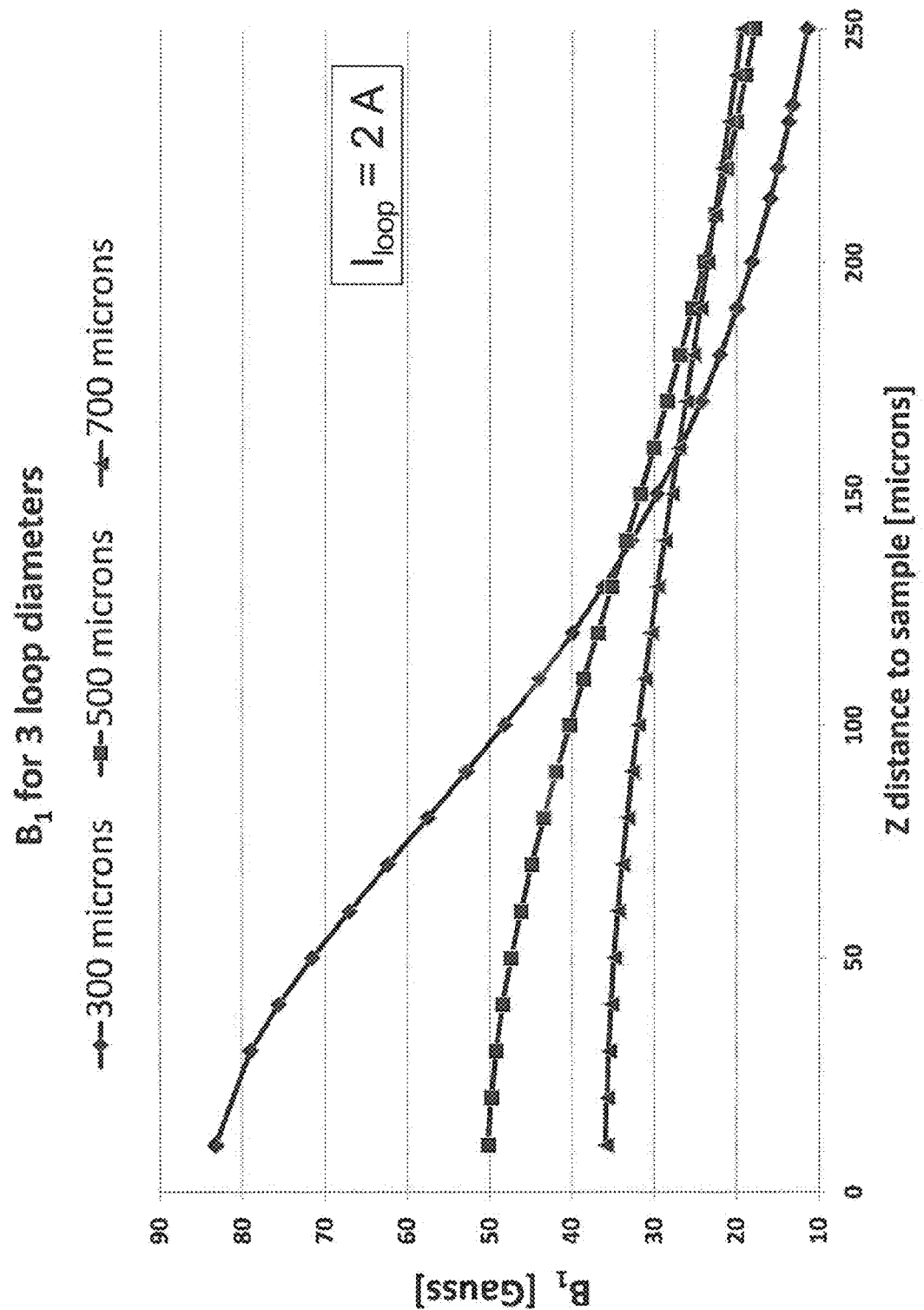
FIG. 14 is a graph displaying the magnetic field value for each loop as a function of separation from the center of the loop to a point along z, (z axis as defined in FIG. 13).

As shown in FIG. 14, the magnetic field $B_{loop}$ due to a loop element of fixed radius decreases in magnitude as the distance from the center of the loop element is increased. If the distance from the loop element is held constant, then the loop element radius which produces the maximum $B_{loop}$ is given by the product of the distance from the loop element center and $\sqrt{2}$. NMR spectroscopy with shuttling based MRFM results in a decrease in $B_1$ delivered to the sample's spins due to the increased distance from the center of the coil if the RF current is held constant. The preferred multiple conductor/antenna embodiments of FIGS. 8-12 improve upon a single conductor/element RF source for use in this case due to the multiple loop-like elements. The inner loop element radius of the current invention can be chosen to produce the largest $B_1$ for the sample-tip distance shown in FIG. 8. The successive outer loops or traces of the multiple conductor design accommodate increasing the sample-tip distance with a smaller decrease in the ratio of the coil's total $B_1$ when the sample is shuttled away for NMR spectroscopy pulse sequence delivery. The larger outer loop elements are optimized for a larger sample-tip separation distance. FIGS. 9 through 11 are representations of planar spiral and nested coil configurations. Many parameters are chosen during fabrication to meet specific application needs. Primary among these parameters are coil density, which is determined by trace wire thickness and spacing between traces, the number of traces and the radius of the inner most and outer most traces. Coil density will determine the maximum $B_1$ for a given coil current and operating distance. Likewise, the trace shapes will also determine the $B_1$ spatial envelope for a given coil current. For the cases of FIGS. 9A, 9B, 10, and 12 the same RF is delivered to all the coils 902A, 902B, 902C through leads 904 and 906, respectively (FIGS. 9A, 9B and 12), and 1002A, 1002B, 1002C through contacts 1004A-C and 1006A-C, respectively (FIG. 10).

For the configuration shown in FIG. 11, a different RF power and/or frequency (from RF sources 105A through 105C) can be delivered through each coil. RF photons of different or equal frequency and power can be delivered simultaneously for each independent coil 1102A, 1102B, 1102C through contacts 1104A-C and 1106A-C, respectively.

In any of the foregoing embodiments, the sample and the magnetic particle can be swapped, such that the sample is coupled to the cantilever and the magnetic particle is replaced with a single particle or an array of magnetic particles secured to a moveable stage.

As used herein the terminology "conductor" refers to an object or type of material which permits the flow of electric charges in one or more directions.

The terminology "multiple conductors" as used herein is intended to encompass, but is not limited to, multiple coils or loops. The multiple loops or coils need not be planar, and may be for example, multiple loops or coils of a spiral conductor. Although the conductors 802A, 802B, appear as loops, the conductors may be of any shape such as, for example, polygonal or may be of an irregular shape such as that depicted in FIG. 6.

As used herein the terminology "trace" refers to the conductive pathways, tracks or signal traces which may be, for example, electrochemically deposited copper patterned onto a non-conductive substrate.

As used herein the terminology "sample" means material, object, thing, specimen, small quantity of something, culture, semiconductor, or the like.

As used herein the terminology "interferometry" refers to a family of techniques in which waves, usually electromagnetic, are superimposed in order to extract information about the waves.

As used herein, the terminology "interferometer" refers to a device or apparatus or portion thereof used for the measurement of small displacements, refractive index changes and surface irregularities. The interferometer may be used in conjunction with continuous wave Fourier transform spectroscopy for analysis of light absorption or emission properties attributable to an identifiable substance or mixture.

As used herein the terminology "spiral" means a. curve on a plane that winds around a fixed center point at a continuously decreasing or increasing distance from the center, or a three-dimensional curve that turns around an axis at a constant or continuously varying distance while moving parallel to the axis, i.e. a helix.

As used herein, a "turn" with respect to a spiral means a loop.

As used herein the terminology "irregular" with respect to shape means not circular, uniform, or symmetrical, and/or having an uneven formation.

As used herein the terminology "processor" includes computer, controller, CPU, microprocessor; multiprocessor, minicomputer, main frame, personal computer, PC, coprocessor, and combinations thereof or any machine similar to a computer or processor which is capable of processing algorithms.

The embodiments described above were chosen and described in order to best explain the principles of the present disclosure and its practical applications, to thereby enable others skilled in the art to best utilize the invention and various embodiments with various modifications as may be suited to the particular use contemplated. The foregoing description of the specific embodiments are intended to reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

Various elements, devices, modules and circuits are described above in associated with their respective functions. These elements, devices, modules and circuits are considered means for performing their respective functions as described herein. While the foregoing is directed to embodiments of the present invention, other and further embodiments of the invention may be devised without departing from the basic scope thereof, and the scope thereof is determined by the claims that follow. Therefore, while the embodiments herein have been described in terms of preferred embodiments, those skilled in the art will recognize that the embodiments herein can be practiced with modification within the spirit and scope of the appended claims.

The invention claimed is:

1. A probe for use in Magnetic Resonance Force Microscopy (MRFM) to provide an image or spectroscopy of a sample comprising:
    a magnetic field source adapted to orient the spin of the nuclei in a sample;
    a detector capable of detecting a magnetic field comprising an oscillator;
    at least one conductor substantially surrounding the oscillator for forming a RF antenna for transmitting a radio frequency electromagnetic field;
    whereby the at least one conductor transmits a radio frequency electromagnetic field that influences the nuclei in the sample, and whereby the detector detects how the nuclei are influenced through the oscillations of the oscillator to provide identification information concerning the content of the sample.

2. The probe of claim 1 wherein the oscillator is a longitudinal oscillator; and wherein the magnetic field source is a magnetic field generator; and wherein the plurality of conductors comprise at least two coils mounted on a silicon substrate having a hole therein to provide the longitudinal oscillator access to a sample's surface; and wherein the at least two coils are adapted to be connected to an RF source; and wherein the longitudinal oscillator operates to detect the change in the angle of the spin from the Zeeman axis of the sample's nuclei or electrons in response to the RF field.

3. The probe of claim 1 wherein the detector comprises a optical fiber adapted to transmit a laser beam; the oscillator comprises a magnetic particle and a reflecting surface which reflects light from a laser beam into the optical fiber to create an interferometer, and whereby the interferometer is used to determine the change in the cantilever's amplitude and/or frequency, which provides information on the angle of spin from the Zeeman axis of the sample's nuclei which provides information relating to the composition of the sample.

4. The probe of claim 1 wherein upon application of an RF pulse sequence to the at least one conductor, the magnetic moments of the sample's nuclei may be rotated so as to reverse the direction of the magnetic moments in the sample's nuclei, and whereby as the magnetic moments in the sample nuclei are rotated, the oscillator resonates at a measurable frequency which is correlated to the composition of the sample.

5. The probe of claim 1 wherein the at least one conductor comprise a series of coils each having first and second terminals which are adapted to be connected to a radio frequency generating source; whereby the sample's nuclei may be concurrently subjected to differing radio frequencies.

6. The probe of claim 1 wherein the at least one conductor is mounted on a substrate which surrounds the oscillator, the substrate having a hole therein for receiving the oscillator.

7. The probe of claim 6 wherein the at least one conductor is formed on the substrate in the form of a spiral having a plurality of turns.

8. A probe for scanning the surface of a sample using magnetic resonance force microscopy comprising:
    a magnetic field source for producing a magnetic field;
    a magnetic sensor comprising a magnetic particle and a support, the magnetic particle being operatively connected to the support;
    an RF antenna at least partially surrounding the magnetic sensor for emitting an RF magnetic field across a portion of the sample; and
    an optical sensor, positioned proximate the magnetic sensor, for detecting displacement of the support,
    whereby the magnetic field from the magnetic field source operates to align the magnetic moments of the sample's nuclei and RF magnetic field operates to vary the alignment of the magnetic moments of the sample's nuclei, the magnetic sensor operating to respond to the variation in the alignments of the magnetic moments and displace the support, the optical sensor operating to sense the displacement of the support to thereby provide information as to the variance of the alignment of the sample's magnetic moments and thereby provide information as to the composition of the sample.

9. The probe of claim 8 wherein the RF antenna comprises a substantially closed loop of wire substantially surrounding the magnetic sensor.

10. The probe of claim 8 wherein the RF antenna comprises a plurality of loops surrounding the magnetic sensor.

11. The probe of claim 8 wherein the optical sensor is located between the RF antenna and the sample.

12. The probe of claim 8 wherein the support is a cantilever, and wherein the magnetic particle responds to the nuclei of the sample causing the cantilever's oscillation amplitude or frequency to change which provides information as to the identification of the sample's content and wherein the magnetic particle is one of a ferro-magnetic, paramagnetic, or superpara-magnetic particle.

13. A method for magnetic resonance force microscopy of a sample comprising:
    providing a probe adapted to scan a surface of an arbitrarily sized sample, the probe comprising a support;
    providing a magnetic sensor operatively associated with the support;
    providing an RF antenna, at least partially surrounding the magnetic sensor, for emitting an RF magnetic field across at least a portion of the sample; the RF antenna adapted to be connected to an RF source for pulsing RF signals to the sample;
    providing an optical sensor, positioned proximate to the magnetic sensor, for detecting displacement of the support element; the optical sensor comprising an interferometer for measuring displacement of the support;
    providing a magnetic field source for generating a background magnetic field for the probe;
    determining information concerning the sample by pulsing an RF field through the RF antenna and,
    using the optical sensor, measuring the movement of the support.

14. The method of claim 13 wherein the RF antenna comprises at least one substantially closed loop of wire surrounding the magnetic sensor, and wherein the support comprises a reflective surface which reflects light from the optical sensor to form an interferometer, the interferometer's laser beams carry information that can be extracted to provide the composition of the sample.

15. The method of claim 14 wherein the RF antenna comprises a plurality of loops surrounding the magnetic sensor.

16. The method of claim 15 wherein the loops are one of irregularly shaped, polygonal, or substantially circular.

17. The method of claim 14 further comprising a display for displaying an image of the atomic level structure of the sample.

18. The method of claim 13 wherein the support element is adapted to be coupled to the sample.

19. The method of claim 13 wherein the support comprises silicon configured as a cantilever, and the magnetic sensor is a magnetic particle operatively associated with the cantilever, and wherein the optical sensor comprises a laser, and wherein laser interferometry tracks the motion of the cantilever which vibrates as magnetic spins of the nuclei or electrons of the sample interact with the magnetic particle, and wherein the cantilever is scanned in three dimensions and the cantilever vibrations produce a three-dimensional image of at least a portion of the sample.

\* \* \* \* \*